(12) United States Patent
Chin

(10) Patent No.: US 7,398,781 B1
(45) Date of Patent: Jul. 15, 2008

(54) METHOD FOR SUBXIPHOID ENDOSCOPIC ACCESS

(75) Inventor: Albert K. Chin, Palo Alto, CA (US)

(73) Assignee: Maquet Cardiovascular, LLC, San Jose, CA (US)

( * ) Notice: Subject to any disclaimer, the term of this patent is extended or adjusted under 35 U.S.C. 154(b) by 0 days.

(21) Appl. No.: 09/635,345

(22) Filed: Aug. 9, 2000

Related U.S. Application Data

(60) Provisional application No. 60/150,737, filed on Aug. 25, 1999, provisional application No. 60/148,130, filed on Aug. 10, 1999.

(51) Int. Cl.
*A61B 19/00* (2006.01)
(52) U.S. Cl. ....................... 128/898; 600/121
(58) Field of Classification Search ............. 128/898; 600/121, 124
See application file for complete search history.

(56) References Cited

U.S. PATENT DOCUMENTS

| | | |
|---|---|---|
| 207,932 A | 9/1878 | Alvord |
| 702,789 A | 6/1902 | Gibson |
| 1,727,495 A | 9/1929 | Wappler |
| 1,867,624 A | 7/1932 | Hoffman |
| 2,011,169 A | 8/1935 | Wappler |
| 2,028,635 A | 1/1936 | Wappler |
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |
| 3,357,433 A | 12/1967 | Fourestier et al. |
| 3,763,806 A | 10/1973 | Shuffield |
| 3,856,016 A | 12/1974 | Davis |

(Continued)

FOREIGN PATENT DOCUMENTS

DE 39 42 589 12/1989

(Continued)

OTHER PUBLICATIONS

Kirklin, JW, et al., "Morphology, Diagnostic Criteria, Natural History, Techniques, Results and Indications" Cardiac Surgery, 2:1695 Ch. 52 Pericardial Disease (1993).

(Continued)

*Primary Examiner*—William H. Matthews
(74) *Attorney, Agent, or Firm*—Fenwick & West LLP

(57) ABSTRACT

Apparatus and method for performing surgical procedures within the mediastinum or within the pericardium include an endoscopic cannula that is introduced into the mediastinum and optionally into the pericardium via a subxiphoid incision. A cavity may be initially dilated for advancing the endoscopic cannula using a dilating tool having an inner cannula and an outer expansible sheath that is expansible to exert a laterally expansive force against the surrounding tissue. Surgical instruments such as a pericardial entry device are inserted into a lumen of the endoscopic cannula to grasp a flap of the pericardium, and a cutting tool is extended to cut the flap to create a small opening through which other surgical tools may be introduced. The endoscopic cannula can then be advanced inside the pericardium to access all regions of the heart by sweeping the endoscopic cannula around the heart. Other surgical instruments may be inserted through the opening to perform surgical procedures within the pericardium.

6 Claims, 17 Drawing Sheets

U.S. PATENT DOCUMENTS

| | | | |
|---|---|---|---|
| 3,870,048 A | 3/1975 | Yoon | |
| 3,877,491 A | 4/1975 | Thastrup | |
| 3,882,854 A | 5/1975 | Hulka et al. | |
| 3,920,024 A | 11/1975 | Bowers | |
| 3,934,115 A | 1/1976 | Peterson | |
| RE29,088 E | 12/1976 | Shaw | |
| 4,022,191 A | 5/1977 | Jamshidi | |
| 4,141,365 A | 2/1979 | Fischell et al. | |
| 4,142,528 A | 3/1979 | Whelan et al. | |
| 4,181,123 A | 1/1980 | Crosby | |
| 4,235,246 A | 11/1980 | Weiss | |
| 4,270,549 A | 6/1981 | Heilman | |
| 4,271,839 A | 6/1981 | Fogarty et al. | |
| 4,291,707 A | 9/1981 | Heilman et al. | |
| 4,318,410 A | 3/1982 | Chin | |
| 4,319,562 A | 3/1982 | Crosby | |
| 4,479,497 A | 10/1984 | Fogarty et al. | |
| 4,493,711 A | 1/1985 | Chin et al. | |
| 4,526,175 A | 7/1985 | Chin et al. | |
| 4,572,548 A | 2/1986 | Porowski et al. | |
| 4,630,609 A | 12/1986 | Chin | |
| 4,662,371 A | 5/1987 | Whipple et al. | |
| 4,765,341 A | 8/1988 | Mower et al. | |
| 4,779,611 A | 10/1988 | Grooters et al. | |
| 4,784,133 A | 11/1988 | Mackin | |
| 4,863,440 A | 9/1989 | Chin | |
| 4,921,483 A | 5/1990 | Wijay et al. | |
| 4,957,477 A | 9/1990 | Lundback | |
| 4,961,738 A | 10/1990 | Mackin | |
| 4,991,578 A | 2/1991 | Cohen | |
| 5,033,477 A * | 7/1991 | Chin et al. | 607/131 |
| 5,071,428 A | 12/1991 | Chin et al. | |
| 5,129,394 A | 7/1992 | Mehra | |
| 5,131,905 A | 7/1992 | Grooters | |
| 5,135,501 A | 8/1992 | Cameron | |
| 5,143,082 A | 9/1992 | Kindberg et al. | |
| 5,150,706 A | 9/1992 | Cox et al. | |
| 5,163,949 A | 11/1992 | Bonutti | |
| 5,183,464 A | 2/1993 | Dubrul et al. | |
| 5,215,521 A | 6/1993 | Cochran et al. | |
| 5,246,014 A | 9/1993 | Williams et al. | |
| 5,256,132 A | 10/1993 | Snyders | 600/16 |
| 5,271,380 A | 12/1993 | Riek et al. | |
| 5,282,811 A | 2/1994 | Booker et al. | |
| 5,313,962 A | 5/1994 | Obenchain | |
| 5,318,589 A | 6/1994 | Lichtman | |
| 5,330,502 A | 7/1994 | Hassler et al. | |
| 5,331,975 A | 7/1994 | Bonutti | |
| 5,334,150 A | 8/1994 | Kaali | |
| 5,336,252 A | 8/1994 | Cohen | |
| 5,339,801 A | 8/1994 | Poloyko et al. | |
| 5,373,840 A | 12/1994 | Knighton | |
| 5,376,076 A | 12/1994 | Kaali | |
| 5,385,156 A * | 1/1995 | Oliva | 128/898 |
| 5,391,156 A * | 2/1995 | Hildwein et al. | 604/174 |
| 5,397,304 A | 3/1995 | Truckai | |
| 5,433,198 A | 7/1995 | Desai | |
| 5,437,680 A | 8/1995 | Yoon | |
| 5,453,094 A | 9/1995 | Metcalf et al. | |
| 5,464,447 A | 11/1995 | Fogarty et al. | |
| 5,482,925 A | 1/1996 | Hutsell | 514/11 |
| 5,489,256 A | 2/1996 | Adair | |
| 5,490,819 A | 2/1996 | Nicholas et al. | |
| 5,496,345 A | 3/1996 | Kieturakis et al. | |
| 5,514,153 A | 5/1996 | Bonutti | |
| 5,540,711 A | 7/1996 | Kieturakis et al. | |
| 5,551,947 A | 9/1996 | Kaali | |
| 5,569,183 A * | 10/1996 | Kieturakis | 604/500 |
| 5,569,291 A | 10/1996 | Privitera et al. | |
| 5,569,292 A | 10/1996 | Scwemberger et al. | |
| 5,571,161 A | 11/1996 | Starksen | |
| 5,591,192 A | 1/1997 | Privitera et al. | |
| 5,601,576 A | 2/1997 | Garrison | |
| 5,601,589 A | 2/1997 | Fogarty et al. | |
| 5,607,441 A | 3/1997 | Sierocuk et al. | |
| 5,613,937 A | 3/1997 | Garrison et al. | |
| 5,613,947 A | 3/1997 | Chin | |
| 5,618,287 A | 4/1997 | Fogarty et al. | |
| 5,630,813 A | 5/1997 | Kieturakis | |
| 5,634,895 A | 6/1997 | Igo et al. | 604/21 |
| 5,650,447 A | 7/1997 | Keefer et al. | 514/772.4 |
| 5,653,722 A | 8/1997 | Kieturakis | |
| 5,653,726 A | 8/1997 | Kieturakis | |
| 5,667,472 A | 9/1997 | Finn et al. | |
| 5,667,520 A | 9/1997 | Bonutti | |
| 5,669,927 A | 9/1997 | Boebel et al. | |
| 5,681,278 A | 10/1997 | Igo et al. | 604/52 |
| 5,685,820 A | 11/1997 | Riek et al. | |
| 5,690,648 A | 11/1997 | Fogarty et al. | |
| 5,695,504 A | 12/1997 | Gifford, III et al. | |
| 5,700,275 A | 12/1997 | Bell et al. | |
| 5,702,343 A | 12/1997 | Alferness | 600/37 |
| 5,702,417 A | 12/1997 | Hermann | |
| 5,707,390 A | 1/1998 | Bonutti | |
| 5,713,950 A | 2/1998 | Cox | |
| 5,716,392 A | 2/1998 | Bourgeois et al. | |
| 5,722,977 A | 3/1998 | Wilhelmy | |
| 5,725,492 A | 3/1998 | Igo et al. | 604/4 |
| 5,728,148 A | 3/1998 | Bostrom et al. | |
| 5,730,756 A | 3/1998 | Kieturakis | |
| 5,738,628 A | 4/1998 | Sierocuk et al. | |
| 5,755,764 A | 5/1998 | Schroeppel | |
| 5,755,765 A | 5/1998 | Hyde et al. | |
| 5,762,604 A | 6/1998 | Kieturakis | |
| 5,772,680 A | 6/1998 | Kieturakis et al. | |
| 5,797,946 A | 8/1998 | Chin | |
| 5,800,449 A | 9/1998 | Wales | |
| 5,810,878 A | 9/1998 | Burel et al. | |
| 5,827,216 A | 10/1998 | Igo et al. | 604/21 |
| 5,860,997 A | 1/1999 | Bonutti | |
| 5,897,586 A | 4/1999 | Molina | |
| 5,900,433 A | 5/1999 | Igo et al. | 514/530 |
| 5,902,331 A | 5/1999 | Bonner et al. | |
| 5,904,711 A | 5/1999 | Flom et al. | |
| 5,931,810 A | 8/1999 | Grabek | 604/51 |
| 5,957,835 A | 9/1999 | Anderson et al. | |
| 5,957,880 A | 9/1999 | Igo et al. | 604/4 |
| 5,972,010 A | 10/1999 | Taheri | |
| 5,972,013 A | 10/1999 | Schmidt | 606/185 |
| 5,972,020 A | 10/1999 | Carpentier et al. | |
| 5,980,548 A | 11/1999 | Evans et al. | |
| 6,007,522 A | 12/1999 | Agro et al. | |
| 6,007,546 A | 12/1999 | Snow et al. | |
| 6,010,531 A | 1/2000 | Donlon et al. | |
| 6,030,406 A | 2/2000 | Davis et al. | |
| 6,036,714 A | 3/2000 | Chin | |
| 6,039,748 A | 3/2000 | Savage et al. | |
| 6,048,337 A | 4/2000 | Svedman | |
| 6,068,621 A | 5/2000 | Balceta et al. | |
| 6,077,218 A | 6/2000 | Alferness | 600/37 |
| 6,080,174 A | 6/2000 | Dubrul et al. | |
| 6,085,754 A | 7/2000 | Alferness et al. | 128/898 |
| 6,095,968 A | 8/2000 | Snyders | 600/16 |
| 6,096,064 A | 8/2000 | Routh | |
| 6,102,046 A | 8/2000 | Weinstein et al. | |
| 6,126,590 A | 10/2000 | Alferness | |
| 6,132,456 A | 10/2000 | Sommer et al. | |
| 6,156,009 A | 12/2000 | Grabek | |
| 6,162,195 A | 12/2000 | Igo et al. | 604/164 |
| 6,165,183 A | 12/2000 | Kuehn et al. | |
| 6,206,004 B1 | 3/2001 | Schmidt et al. | |
| 6,237,605 B1 * | 5/2001 | Vaska et al. | 128/898 |
| 6,267,763 B1 | 7/2001 | Castro | |
| 6,287,250 B1 | 9/2001 | Peng et al. | |

| | | | |
|---|---|---|---|
| 6,315,778 B1 | 11/2001 | Gambale et al. | |
| 6,322,536 B1 | 11/2001 | Rosengart et al. | |
| 6,346,074 B1 * | 2/2002 | Roth | 600/121 |
| 6,428,556 B1 | 8/2002 | Chin | |
| 6,461,333 B1 | 10/2002 | Frezza | |
| 6,463,332 B1 | 10/2002 | Aldrich | |
| 6,478,028 B1 | 11/2002 | Paolitto et al. | |
| 6,488,689 B1 | 12/2002 | Kaplan et al. | |
| 6,530,933 B1 | 3/2003 | Yeung et al. | |
| 6,569,082 B1 | 5/2003 | Chin | |
| 6,607,547 B1 | 8/2003 | Chin | |
| 6,612,978 B2 | 9/2003 | Lau et al. | |
| 6,689,048 B2 | 2/2004 | Vanden Hoek et al. | |
| 6,697,677 B2 | 2/2004 | Dahl et al. | |
| 6,702,732 B1 | 3/2004 | Lau et al. | |
| 6,706,052 B1 | 3/2004 | Chin | |
| 6,835,193 B2 | 12/2004 | Epstein et al. | |
| 6,851,722 B2 | 2/2005 | Chiu et al. | |
| 6,889,091 B2 | 5/2005 | Hine et al. | |
| 2001/0047170 A1 | 11/2001 | Branco | |
| 2002/0035361 A1 | 3/2002 | Houser et al. | |
| 2002/0052602 A1 | 5/2002 | Wang et al. | |
| 2002/0058925 A1 | 5/2002 | Kaplan et al. | |
| 2002/0111637 A1 | 8/2002 | Kaplan et al. | |
| 2002/0173622 A1 | 11/2002 | Wettstein et al. | |
| 2002/0177207 A1 | 11/2002 | Sugiyama et al. | |
| 2003/0212446 A1 | 11/2003 | Kaplan et al. | |

FOREIGN PATENT DOCUMENTS

| | | |
|---|---|---|
| EP | 0095727 A1 | 12/1983 |
| EP | 0 642 764 | 9/1994 |
| EP | 0791330 A2 | 8/1997 |
| FR | 1 370580 | 12/1962 |
| GB | 2 082 459 | 8/1981 |
| GB | 2 195 540 | 9/1987 |
| SU | 510235 | 4/1976 |
| SU | 1371689 | 3/1986 |
| WO | WO 96/00038 | 1/1996 |
| WO | WO 96/32882 | 10/1996 |
| WO | WO 97/26831 * | 7/1997 |
| WO | WO 98/24378 | 6/1998 |
| WO | WO 98/24488 A2 | 6/1998 |
| WO | WO 98/24488 A3 | 6/1998 |
| WO | WO 99/13785 | 3/1999 |
| WO | WO 99/13936 | 3/1999 |
| WO | WO 00/40159 A1 | 7/2000 |

OTHER PUBLICATIONS

Sabiston DC Jr., et al., Atlas of Cardiothoracic Surgery, "41 Pericardial Window", 1st Ed. pp. 235-237 (1995).
Grandjean JG, et al., "Coronary Reoperation via Small Laparatomy Using Right Gastroepiploic Artery Without CPB", Society of Thoracic Surgeons 61:1853-5 (1996).
Benetti FJ, et al, "Video Assisted Coronary Bypass Surgery", J. Card Surg 10:620-625 (1995).
Bartoccioni S., et al., "Laparaoscopic Harvesting of Right Gastroepiploic Artery for Coronary Artery Bypass Graft Performed Without Sternotomy" European Assoc. of Card. Surg. (abstract) 201 EACTS Abstracts (1998).
A New Approach: Access the Pericardial Space with the PerDUCER Pericardial Access Device, CoMEDICUS Incorporated.
Spodick, D.H., et al., "Clinical Update: IPTD: Intrapericardial Therapeutics and Diagnostics: The PerDUCER Permits Direct Access to the Heart" Cath-Lab Digest 7: (9) :12 (Sep. 1999).
Simonsen, M., Ph.D., "Researchers undaunted by setbacks i nthe angiogenesis sector", Cardiovascular Device Update 5:(5) (May 1999).
Diane Kaminski, Medical Industry Today, Device and Diagnostics, Medical Data International, Inc. p. 1-2 (Sep. 23, 1998).
Spodick, D. H., "Directly Applied Cardiac Therapy: Experts Explore Potential Benefits", Internal Medicine World Report, 3:(11) (1998).
For Immediate Release: Comedicus Gets Approval to Sell Product in European Union, Comedicus Incorporated, (Mar. 1, 1999).
Comedicus Incorporated Update—Oct. 1999.
The 4th International Symposium on Intrapericardial Therapeutics and Diagnostics (IPTD) (Mar. 6, 1999).
P.J. de Feyter et al., "Permanent Cardiac Pacing with Sutureless Myocardial Electrodes: Experience in First One Hundred Patients," Pace, vol. 3, No. 2, Mar. 1980, pp. 144-149.
S. Stewart, M.D., "Placement of the Sutureless Epicardial Pacemaker Lead by the Subxiphoid Approach," The Annals of Thoracic Surgery, vol. 18, No. 3, Sep. 1974, pp. 308-313.
L. Watkins, Jr., M.D. et al., "Implantation of the Automatic Defibrillator: The Subxiphoid Approach," The Annals of Thoracic Surgery, vol. 34, No. 5, Nov. 1982, pp. 515-520.
R. Broadman et al., "ICD Implantation via Thoracoscopy, "Mailslot" Thoracotomy and Subxiphoid Incision," The Annals of Thoracic Surgery, vol. 57, No. 2, Feb. 1994, pp. 475-476.
M. Zenati, M.D. et al., "Left Heart Pacing Lead Implantation Using Subxiphoid Videopericardioscopy," J. Cardiovasc Electrophysiol, vol. 14, Sep. 2003, pp. 949-963.
Bernhard, Victor M. et al., "Cardiovascular Endoscopy: Historical Perspectives", Endovascular Surgery, 1989 W.B. Saunders Company, pp. 13-30.
Carpentier, A., "Technique d'implantation de pace-maker par une voie d'abord abdominale sous-xyphoidienne," La Presse Medicale, Masson et Cie, Editeurs, Paris, vol. 76, No. 2, Jan. 13, 1968, 2 pp.
Comedicus Incorporated, Equity Investment Information Sheet, May 17, 1999.
Delaria, G.A. et al., "Leg Wound Complications Associated With Coronary Revascularization", J.Thorac, Cardiovasc. Surgery, 81:403-407, 1981.
Dimitri, W.R., et al., "A Quick and Atraumatic Method of Autologous Vein Harvesting Using the Subcutaneous Extraluminal Dissector", J. Cardiovasc. Surg., 28:103-11, 1987.
Fogarty, M.D., Thomas J., et al., "Selected Applications of Balloon Dissection", pp. 45-52.
Fontenelle, Larry, J., "Subxiphoid Pericardial Window", Thoracic and Cardiovascular Surgery, The American Association for Thoracic Surgery, Jul. 1971, vol. 62, No. 1, pp. 95-97.
Hauer, G., et al. "Endoscopic Subfascial Discussion of Perforating Vein", Surg. Endos. 2:5-12, 1988.
"Incision Decision", Atrium Medical Corporation advertisement, appearing in J. Thorac. Cardiovasc. Surg., 83(4), 1982.
Levin, Bradley H., "The Subxiphoid Pericardial Window", Surgery, Gynecology & Obstetrics, Dec. 1982, vol. 155, pp. 804-806.
Meldrum-Hanna, W. et al., "Long Saphenous Vein Harvesting," J. Surg., 56: 923-924, 1986.
Moazami, N., M.D. et al., "Minimally Invasive Greater Saphenous Vein Harvesting For Coronary Artery Bypass Surgery", Mar. 1997, pp. 94-98.
Prager, Richard L., et al., "The Subxiphoid Approach to Pericardial Disease", The Annals of Thoracic Surgery, vol. 34, No. 1, Jul. 1982.
Rashid, A., et al., "Subcutaneous Technique for Saphenous Vein Harvest", Ann. Thorac. Surg., 37(2):169-170, 1984.
Santos, Gil H., et al., "The Subxiphoid Approach in the Treatment of Pericardial Effusion", Albert Einstein College of Medicine, Sep. 21, 1976, pp. 467-470.
"Saphenous Vein Grafts Are No. 1. Period," Atrium Medical Corporation advertisement, appearing in J. Thorac. Cardiovas. Surg., 82(6), 1981.
Wheatley, D.J., M.D., ed., "Surgery of Coronary Artery Disease", C.V. Mosby Company, pp. 348-349, pp. 374-375.
International Search Report and Written Opinion, PCT/US04/00859, Jun. 20, 2005.
PCT International Search Report and Written Opinion; PCT/US04/34538, Nov. 3, 2005, 10 pages.
PCT International Search Report and Written Opinion, PCT/US04/00760, Sep. 27, 2006, 7 pages.
PCT International Search Report and Written Opinion, PCT/US04/22137, Jul. 9, 2007, 8 pages.
Myers, E. L. et al., "Tsg101, an Inactive Homologue of Ubiquitin Ligase E2, Interacts Specifically with Human Immunodeficiency Virus Type 2 Gag Polyprotein and Results in Increased Levels of Ubiquinated Gag", Nov. 2002, pp. 11226-11235, vol. 76, No. 22, Journal of Virology, Cambridge, England.

PCT International Search Report and Written Opinion; PCT/US04/00760, Jul. 6, 2005, 7 pages.

PCT Notification Concerning Transmittal of Copy of International Preliminary Report on Patentability; PCT/US2004/00760, Aug. 25, 2005, 5 pages.

* cited by examiner

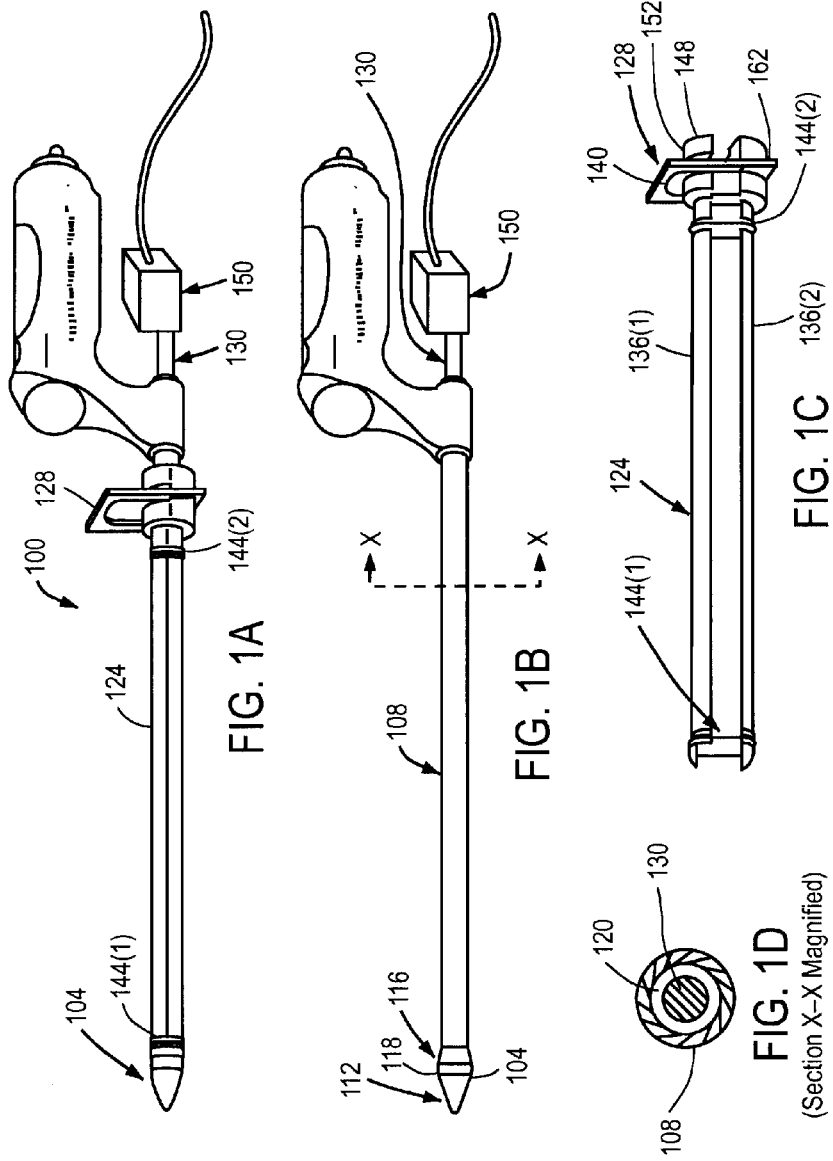

(Section A-A Magnified)

METHOD FOR SUBXIPHOID ENDOSCOPIC ACCESS

CROSS-REFERENCE TO RELATED APPLICATIONS

This application claims priority from provisional applications 60/150,737 filed Aug. 25, 1999, and 60/148,130, filed Aug. 10, 1999, each of which are hereby incorporated by reference in their entirety.

BACKGROUND OF THE INVENTION

1. Field of the Invention

The present invention relates to apparatus and methods for performing minimally invasive surgery. More particularly, the invention relates to a method of accessing the mediastinum and the pericardium using a single subxiphoid incision, and using an endoscopic cannula to access all regions of the heart.

2. Description of the Related Art

Several different incisions have traditionally been used to access mediastinal organs, such as the heart (surrounded by the pericardium), the esophagus, and lymphatic glands. Examples of such incisions are sternotomy (a division of the patient's sternum) thoracotomy (an incision between two adjacent ribs) and a subxiphoid incision to create a pericardial window by exposing and excising a portion of the pericardium. For example, a subxiphoid incision has been made to allow excision of the xiphoid, and retraction of the sternum upward to expose the anterior pericardium.

These procedures, however, are all quite invasive, requiring large incisions or open heart surgery. Thoracotomy is additionally invasive as it requires the deflation of one or both lungs, since the approach is via the pleural cavity. Nevertheless, when it is desirable to access other regions of the heart than merely its anterior region, the current practice is to employ these invasive methods to dislodge the heart from its resting place within the pericardium, so that all regions of the heart may be accessed and cardiac procedures performed. For example, to access both left and right sides of the heart, as well as the posterior and anterior regions, surgeons are currently using a partial or full sternotomy (i.e. a partial or full division of the patient's sternum) to gain access to the several regions of the heart by permitting the heart to be rotated or lifted out of its resting place in the chest. Such a procedure, however, is too invasive, and thus not desirable.

With the advent of minimally invasive surgery, approaches have been developed using smaller access incisions or ports. Coronary bypass surgery has been performed on the beating heart through direct incisions in the chest and abdomen, including sternotomies and thoracotomies. A subxiphoid incision has been used to anastomose a gastroepiploic artery to the posterior descending coronary artery for coronary artery bypass. These procedures, however, have been performed under direct vision, and thus still require a fairly large incision to assist the surgeon in observing the field of surgery.

To achieve even less invasive surgery, it is desirable to perform cardiac procedures endoscopically. Endoscopic coronary bypass surgery has been performed on a stopped heart following the institution of cardiopulmonary bypass. In this procedure, ports are placed in the intercostal spaces, through the chest wall, to allow placement of the endoscope and operating instruments. This method, however, does not enable the surgeon to access all regions of the heart. With port access surgery or beating heart surgery from a limited thoracotomy, only one side of the heart is accessible. For example, with a left thoracotomy or the introduction of left side ports, surgery is limited only to the left side of the heart. Endoscopic harvesting of the gastroepiploic artery for coronary artery bypass surgery has also been described, involving standard laparoscopic techniques of gas insufflation and introduction of laparoscopic forceps, scissors, and staplers. However, none of these minimally invasive methods allow access to all regions of the heart. Thus, a method and apparatus are needed to allow safe and minimally invasive access to all regions of the heart for performing cardiac procedures.

In addition, conventional procedures such as open heart surgery, port-access surgery using trocar ports and an endoscope, or beating heart surgery through a partial sternotomy or thoracotomy, all require making a large incision in the pericardium to expose the heart. In the prior art, methods of accessing the heart to perform cardiac procedures involved making an incision in the pericardium using a sharp-edged instrument through an incision in the chest. As the heart typically underlies the pericardium contiguously, the surgeon is presented with the difficult task of incising the pericardium without accidentally cutting the heart. To avoid this difficulty during port-access surgery, a second incision into the skin is also required to allow the insertion of forceps to pull the pericardium away from the heart. This allows the incision of the pericardium to be executed more safely. However, this technique requires multiple incisions in the patient and requires the advancement of multiple instruments in separate passageways to the pericardium.

In addition to requiring several incisions, the conventional techniques also typically require the incision in the pericardium to be lengthy. The sharp-edged instrument must slice a cut of sufficient length to allow the insertion of other surgical tools into the pericardium. At the end of the cardiac procedure, it is desirable to close the pericardial incision if possible, to reduce fibrous adhesions to the heart and pericarditis. With endoscopic port-access surgery, a long pericardial incision is difficult to close, due to the complexity of endoscopic suturing.

Another problem arising in conventional cardiac procedures is the dissection of a working tunnel from the initial incision to the pericardium. Mechanical probing of heart tissue may cause severe or dangerous cardiac arrhythmias such as ventricular fibrillation. Therefore, it is desirable to use a small dilating instrument to create the initial tunnel. However, the instruments currently available to perform cardiac procedures are typically large, and therefore a larger cavity must be dissected to allow these instruments to pass through to the pericardium. Although using a larger dilator may create the necessary space, a larger dilator may cause damage to the heart by causing cardiac arrhythmias as discussed above. If a smaller dilator is used to minimize this potential trauma, the working cavity may not be large enough to allow the larger instruments required in the procedure to be advanced to the pericardium. A further problem with conventional dilators such as balloon dissectors is that such tools exert shear force on the surrounding tissue as they are advanced in the body. Shear force has a tendency of causing vessel avulsion and tissue abrasion.

Various other schemes and devices have been previously devised in an attempt to enter the pericardium via a small portal of entry, or via a percutaneous puncture site. None of these systems permit reliable, safe entry under direct, endoscopic visualization. U.S. Pat. No. 5,931,810 (Grabek) describes a grasping instrument with jaws that grasp the pericardium followed by advancement of a needle through a bore in the shaft of the instrument. The needle extends between the closed jaws of the device, into the pericardium. This concept suffers from unreliability, as it is difficult to ensure that the needle will pierce between two layers of pericardium that are compressed by the jaws of the device, without an active technique of holding the two opposed layers of pericardium apart. Thus, as there is no central cavity in a flap of pericardium grasped by the instrument jaws, a needle advanced down a central bore of the instrument may easily end up outside of the pericardium, or embedded in the pericardium, instead of lying between the two layers of pericardium pinched together by the jaws. Also, axial advancement of the needle carries the potential of myocardial puncture. Needle entry with the Grabek device must be verified by subsequent passage of a guidewire into the pericardial sac, or by infusion of fluid or contrast material through the needle into the pericardial cavity.

U.S. Pat. No. 5,827,216 (Igo et al.) and U.S. Pat. No. 5,972,013 (Schmidt) both describe tubes that are placed in contact with the pericardium, applying a vacuum to pull a bleb of tissue into the tube, followed by penetration of the pericardial bleb with a needle. These techniques are unreliable, because there is generally a layer of fatty tissue adherent to the pericardial surface, and suction may pull fat into the tube instead of pericardium.

U.S. Pat. No. 5,071,428 (Chin et al.) describes a clamp with distal points that grasp a flap of pericardium, allowing a guidewire to be advanced within tubular guides to puncture through the pericardium. A tube may follow the guidewire into the intra pericardial space. This design may cause myocardial trauma due to the sharp pointed grasping clamp. The multiple steps of pericardial grasping, pericardial puncture, guidewire advancement, and catheter insertion render this technique impractical.

Therefore, apparatus and methods are needed to provide safe and minimally invasive access to all regions of the heart during cardiac procedures, requiring a minimum number of incisions, and without requiring a long incision either for initial access or at the pericardium. The proposed technique of this application allows reliable and safe entry into the pericardium under continuous endoscopic visualization.

SUMMARY OF INVENTION

Apparatus and methods for using the apparatus are disclosed for providing safe and minimally invasive access to mediastinal structures, including the heart surrounded by the pericardium. More specifically, the apparatus and methods are directed to accessing the pericardium via a subxiphoid approach, accessing the heart within the pericardium, and performing cardiac procedures thereon.

The surgical apparatus preferably used for performing the surgical method of this invention is an endoscopic cannula comprising a cannula, a transparent tip located at the distal end of the cannula, and an endoscope preferably positioned at the distal end of the cannula. The cannula has at least one lumen, and one or more additional lumens for advancement of surgical tools. The transparent tip is preferably tapered to provide better visualization by offsetting and retracting tissue away from the field of view. Still more preferably, the transparent tip has a generally conical shape. The transparent tip is preferably removable and replaceable, such that it may be removed when it is desired to obtain a sharper image of the surgical site.

In a preferred embodiment, the endoscopic cannula may comprise an access port positioned at a proximal end of the cannula, for receiving surgical instruments into an instrument lumen of the cannula. Such a preferred endoscopic cannula further comprises an endoscopic eyepiece, skewed relative to the proximal end of the endoscope, for facilitating the viewing of a surgical site through the endoscope while minimizing interference with surgical instruments introduced into the cannula.

In an alternative embodiment, the cannula of the endoscopic cannula is articulable, and the cannula further comprises a wire lumen, a wire, and an articulating lever. The wire is positioned within the wire lumen, having a distal end attached to a distal end of the cannula. The articulating lever is positioned near the proximal end of the cannula, attached to the proximal end of the wire, for tensioning the wire in a first position to cause the distal end of the cannula to bend away from alignment with the proximal end of the cannula, and for relaxing the wire in a second position to position the distal end of the cannula substantially aligned with the proximal end of the cannula.

Using the methods of this invention, the endoscopic cannula is either directly advanced to the mediastinum or alternatively, a cavity is first dilated and the endoscopic cannula is advanced through the dilated cavity. Once the endoscopic cannula is advanced into the mediastinum, surgical tools are advanced through the one or more additional lumens acting as access ports, and surgical procedures are performed within the mediastinum. In directly advancing the endoscopic cannula, the endoscopic cannula is inserted directly into the initial subxiphoid incision and is guided, under endoscopic visualization, to the surgical site. Alternatively, a cavity toward the surgical site may be first dilated using a dilation tool according to this invention, and the cannula may be subsequently advanced within the dilated cavity. The second method is advantageous because as the dilation tool generally has a smaller diameter than the endoscopic cannula, initially inserting the dilation tool minimizes trauma to the heart and reduces the chance of ventricular fibrillation due to irritation of the heart with a large diameter instrument.

The dilation tool optionally used to dilate a cavity for the endoscopic cannula has an inner cannula having an elongated body, a transparent tip at the distal end of the elongated body, an endoscope, and an outer expandable sheath. Preferably, the dilation tool has a small maximal dimension which minimizes trauma to the pericardium upon reaching the pericardium. The inner cannula has a tip having an enlarged region positioned distal to a distal end of the outer expandable sheath. The inner cannula is withdrawn through the outer expandable sheath, and the expandable sheath dilates a cavity concurrent to the retraction of the tip. The expandable sheath exerts a radial force against the surrounding tissue as the tip is retracted through the sheath. The radial force provides a less traumatic dilation than conventional dilation techniques such as using a bougie dilation, in which shear force is directly applied to surrounding tissue.

Once the cavity is dilated, the endoscopic cannula is then inserted into the incision and advanced into the proximal end of the expandable sheath. As the endoscopic cannula is advanced to the pericardium through the sheath, it will also cause the expandable sheath to expand further and dilate the working tunnel to a sufficient size to accommodate the endoscopic cannula. The expandable sheath provides the additional benefit of guiding the endoscopic cannula to the proper position at the pericardium. Alternatively, the endoscopic cannula is inserted directly into the initial incision without dilation.

Where the endoscopic cannula is used to perform cardiac procedures within the pericardium, a tool is needed to incise an opening into the pericardium for inserting the endoscopic cannula into pericardium. A preferred tool to be inserted into the lumen of the endoscopic cannula for providing entry through the pericardium is a pericardial entry instrument in accordance with the present invention. The pericardial entry instrument includes a grasping tool for gripping a portion of the pericardium, and a cutting tool slidably disposed on the outside of the grasping tool for cutting the gripped portion of the pericardium. In a preferred embodiment, the pericardial entry instrument is utilized under endoscopic visualization. The pericardial entry instrument is advanced through a lumen of the endoscopic cannula and toward the pericardium, where it is then used to cut an opening into the pericardium for advancing other surgical tools into the pericardium.

In a preferred method, the pericardial entry device is advanced tangentially to the pericardium to allow the grasping tool to grasp a flap of the pericardium without endangering the underlying heart. Once a flap of the pericardium is grasped, the cutting tool is extended to the cut the flap, creating a small opening into which other surgical tools may be introduced. In a preferred embodiment, the cutting tool is a tubular cutting device which creates a circular opening which facilitates the introduction of other surgical tools. Due to the small circumference of the tubular cutter, the opening in the pericardium is also small. One embodiment of a method of performing a cardiac procedure used in conjunction with the described apparatus comprises first making a single subxiphoid incision to provide initial access into the patient's body, inserting an endoscopic cannula into the incision, advancing the endoscopic cannula to the mediastinum under endoscopic visualization, and performing the surgical procedure with the mediastinum. Optionally, the method further includes initially providing a dilated cavity for passing the endoscopic cannula into the mediastinum as previously described, and performing the surgical procedure within the mediastinum.

As the pericardium, enclosing the heart, resides in the mediastinum, one major application of the methods according to the present invention is for performing cardiac procedures within the pericardium. For these procedures, the endoscopic cannula is advanced under endoscopic visualization, as described previously, either directly into the initial subxiphoid incision or after first dilating a cavity using a dilation tool as described herein. Upon reaching the pericardium, a flap of the pericardium is gripped using a pericardial entry instrument as described herein, and the flap is cut to create an opening in the pericardium. Alternatively, the pericardial entry instrument may be aligned substantially tangentially to the pericardium under endoscopic visualization in gripping a flap of the pericardium. In cutting the pericardium, this invention contemplates cutting the flap of the pericardium away from the underlying heart.

The subxiphoid approach method is particularly advantageous as it enables the surgeon to access all regions of the heart, that is a 360 degree access capability including the anterior, posterior, left and right regions of the heart. Using one embodiment of this method, the cannula is initially inserted into the pericardium via an incision near the apex of the heart and then swept over the anterior and posterior surfaces of the heart. It should be noted that while entry near the apex of the heart aids the surgeon by providing a landmark for easier recognition of the position of the endoscopic cannula within the body, such an entry is not required by this invention and other entry positions, such as entry in the posterior region of the heart, are also contemplated. Once inside the pericardium, the cannula can be maneuvered around the heart substantially because of the subxiphoid entry and the flexibility of soft tissue around the heart. Thus, all regions of the heart may be accessed without the need for invasively lifting or rotating the heart to access posterior or lateral vessels and structures.

The subxiphoid access method is quite advantageous over conventional methods. As this procedure is performed under endoscopic visualization it is minimally invasive. In addition, as the approach is through a subxiphoid incision, there is no need to go through the pleural cavity and thus no need to deflate the lungs. Also, although the method requires only a single incision (that is, the subxiphoid incision), using this method access is gained to all regions of the heart. Conventionally, such extensive access to the heart has only been possible using invasive methods such as pericardial window, open heart surgery, or port access surgery using several incisions and ports. Thus, using the subxiphoid access method as herein described, the surgeon may access all regions of the heart with a single incision, without needing to go through the pleural cavity.

In particular, the subxiphoid access methods of this invention are advantageous over the methods disclosed in the Grabek, Igo and Schmidt patents. As described above, the Grabek method is unable to reliably enter the pericardium, as there is no central cavity in a flap of pericardium grasped by the instrument jaws, and needle entry with the Grabek device must be verified. In contrast, the instrument of this application uses a tube to cut along a flap of pericardium grasped by jaws, under direct visualization. There is no ambiguity regarding success or failure of the pericardial entry, as the pericardial hole is observed as it occurs. The methods disclosed in Igo and Schmidt both employ vacuum to grasp the pericardium into a tube, followed by needle entry into the pericardial bleb formed by the vacuum. Both of these schemes inherit the deficiency of the Grabek device, with its unreliable needle entry. In addition, these two schemes find it difficult to form a bleb of pericardium in the clinical situation. The great majority of human patients have a layer of fatty tissue adherent to the pericardial surface. Suction devices, particularly those used in a percutaneous manner under fluoroscopic guidance, will pick up fat rather than pericardium, leading to unsuccessful pericardial needle entry.

In the device of the present application, the endoscopic cannula with the transparent tapered tip is used to bluntly dissect a path to the pericardium, through the fat and connective tissue. Direct visualization allows verification that the pericardial surface is clean and devoid of adherent fat. Application of the pericardial entry instrument may occur under visual guidance on an exposed pericardial surface.

While the methods according to the present invention are substantially described with reference to performing cardiac procedures within the pericardium, the invention is not limited to those procedures only. In an alternative embodiment of the method, after making the subxiphoid incision and inserting the endoscopic cannula in the incision, the endoscopic cannula is advanced to the mediastinum under endoscopic visualization. The surgical procedure is then performed on structures, other than the heart, that are located within the mediastinum, for example the esophagus and the lymphatic glands. For example, a biopsy may be taken from a lymphatic gland using this procedure.

BRIEF DESCRIPTION OF THE DRAWINGS

FIG. 1A is a perspective view illustrating a dilation tool in accordance with the present invention.

FIG. 1B is a perspective view illustrating the inner cannula of a dilation tool in accordance with the present invention.

FIG. 1C is a perspective view illustrating the expandable sheath of a dilation tool in accordance with the present invention.

FIG. 1D is a cross sectional view of the inner cannula of a dilation tool in accordance with the present invention.

DETAILED DESCRIPTION OF THE PREFERRED EMBODIMENTS

Figure 1E:
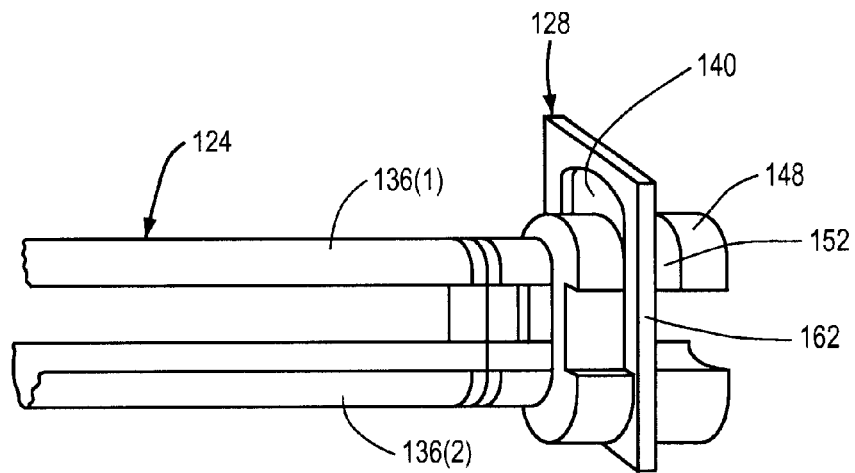
FIG. 1E is a perspective view illustrating an embodiment of the slide mount in accordance with the present invention.

FIGS. 1A-D illustrate a preferred embodiment of a dilation tool 100 which embodies an aspect of the invention. Dilation tool 100 includes an inner cannula 108 having lumen 120 as shown in FIG. 1D, and an expandable sheath 124 comprised of shells 136(1) and 136(2) as shown in FIG. 1C. Preferably, the inner cannula is formed of a sufficiently rigid material, such as metal or plastic, that would allow tip 104 to be used to bluntly dissect a cavity from an incision point to the pericardium or other surgical site of interest. Lumen 120 is provided to allow the insertion of an endoscope 130 fitted with video camera 150 in the dilation tool 100, and tip 104 is transparent to allow endoscopic visualization during the surgical procedure. In a preferred embodiment, tip 104 has a long distal taper 112 as shown in FIG. 1B, which allows tip 104 to bluntly dissect away tissue encountered along the cavity to the pericardium. Tapered tip 104 also provides a broader and less distorted field of view than conventional tips. Tip 104 in the preferred embodiment also has a proximal short taper 116. The proximal short taper 116 facilitates the retraction of the inner cannula 108 through expandable sheath 124. Intermediate between proximal short taper 116 and long distal taper 112 is an optional enlarged region 118. The enlarged region 18 has a maximal dimension greater than the diameter of the inner rigid cannula 108, and this greater maximal dimension causes the expandable sheath 124 to expand as tip 104 is retracted through sheath 124. Tapered tip 104 is preferably configured to be removable from the elongate body, for example by means of being screwed into a threaded end of the elongate body or by snapping to fit onto the elongate body.

Inner cannula 108 preferably has a relatively small diameter, for example 7 mm, which minimizes the probing force exerted on the heart caused by advancement of the dilation tool 100 to the anterior surface of the pericardium. The use of larger cannulas to isolate the anterior surface of the pericardium has a greater tendency to cause cardiac arrhythmias. However, in order to introduce pericardial puncture or entry instruments to the surgical site, an endoscopic cannula with an access port must be advanced to the pericardium, and these cannulas typically have larger diameters, for example 12 mm in diameter. Therefore, a cavity is preferably initially dilated to accommodate these larger cannulas.

In use of tool 100, as shown in FIG. 1A, expandable sheath 124 resides on the outside of inner cannula 108. Expandable sheath 124 allows insertion into the body of instruments of a diameter greater than the initial puncture size. In a preferred embodiment, as shown in FIG. 1C, the expandable sheath 124 is generally rigid and is split longitudinally into two shells 136(1) and 136(2). The expandable sheath 124 may be metal, plastic, or the like. Metal expandable sheaths may provide better dilation than plastic due to their superior rigidity.

Expandable sheath 124 has two resilient connectors 144, a first resilient connector 144(1) near the proximal part of the sheath 124 and a second resilient connector 144(2) near the distal end of the sheath 124. The resilient connectors 144 are preferably elastic bands and contract the two shells 136(1) and (2) against inner cannula 108. The resiliency of connectors 144 allows expandable sheath 124 to expand along the longitudinal split as an object of greater diameter is advanced or withdrawn through sheath 124. In one embodiment, the inner surface of the distal end of the expandable sheath 124 is chamfered to facilitate easier removal of the tip 104 through the expandable sheath 124. The proximal end of the expandable sheath 124 is attached to slide mount 128 which retains shells 136(1) and (2) of expandable sheath 124 in axial alignment as sheath 124 expands. Slide mount 128 is preferably composed of a hard plastic or other rigid material having a slot 140 disposed to fit in tracts or grooves in the proximal ends of the expandable sheath 124.

Figure 1F:
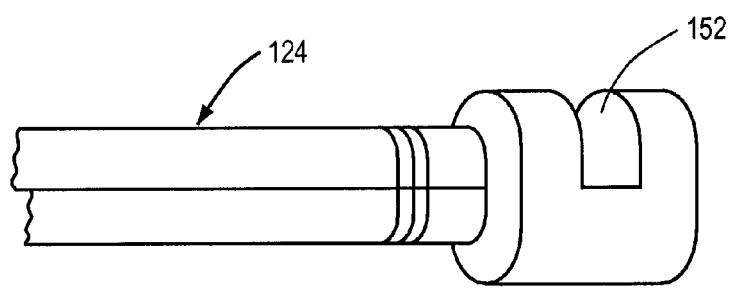
FIG. 1F is a perspective view illustrating an embodiment of the housing in accordance with the present invention.

In a preferred embodiment, one shell of the expandable sheath 124, lower shell 136(2) in FIG. 1C, is attached to the slide mount 128. The other shell, upper shell 136(1) in FIG. 1C, is unattached, and is constrained to slide freely in a vertical direction within the slot 140. In one embodiment, axial alignment is maintained due to use of a housing 148. In this embodiment, shown in FIG. 1E, the unattached shell 136(1) has a housing 148 disposed at its proximal end. As shown in FIGS. 1E and 1F, housing 148 has a horizontal dimension greater than the horizontal dimension of the slot 140. However, housing 148 has a groove 152 which receives frame 162 of the slide mount 128, such that housing 148 is slidably movable within groove 152 in the vertical direction. Groove 152 has a sufficiently narrow width to ensure minimal axial movement of shell 136(1) relative to frame 162. Thus, during advancement or retraction of a device, the unattached shell 136(1) is displaced vertically, but its axial movement is restricted.

Figure 2:
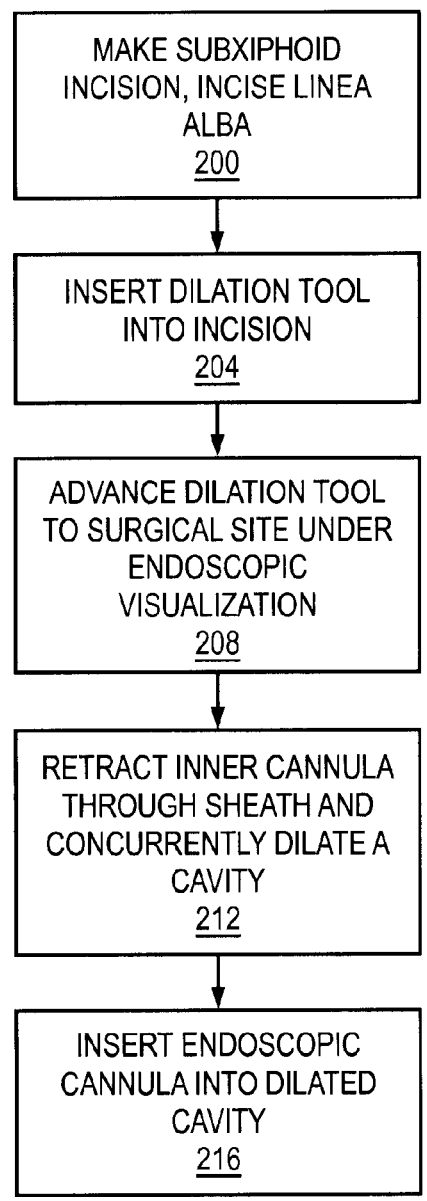
FIG. 2 is a flow chart illustrating a method of using the dilation tool accordance with the present invention.

FIG. 2 is a flowchart which illustrates a method of using dilation tool 100, and will be described with reference to FIGS. 3A-3D, showing only the apparatus. Step 200 involves the making of a subxiphoid incision overlying an entry point for a surgical procedure. The subxiphoid incision is preferably small, about 2 cm. Next, the subcutaneous tissue below the incision is bluntly dissected to expose the linea alba, which is also incised. In step 204, dilation tool 100 is inserted into the incision, and tapered tip 104 bluntly dissects a cavity responsive to the advancement of the dilation tool 100. Dilation tool 100 is then positioned on the posterior aspect of the xiphoid process and sternum. In step 208, dilation tool 100 is advanced within the mediastinum (optionally to the pericardium) under endoscopic visualization. A laparoscopic endoscope with an attached CCD chip camera can be used to accomplish endoscopic visualization. Since the pericardium is a thin membrane, visualization of the beating heart through the endoscope underneath a translucent membrane indicates correct positioning of the dilation tool 100 on the anterior surface of the pericardium.

Figure 3:
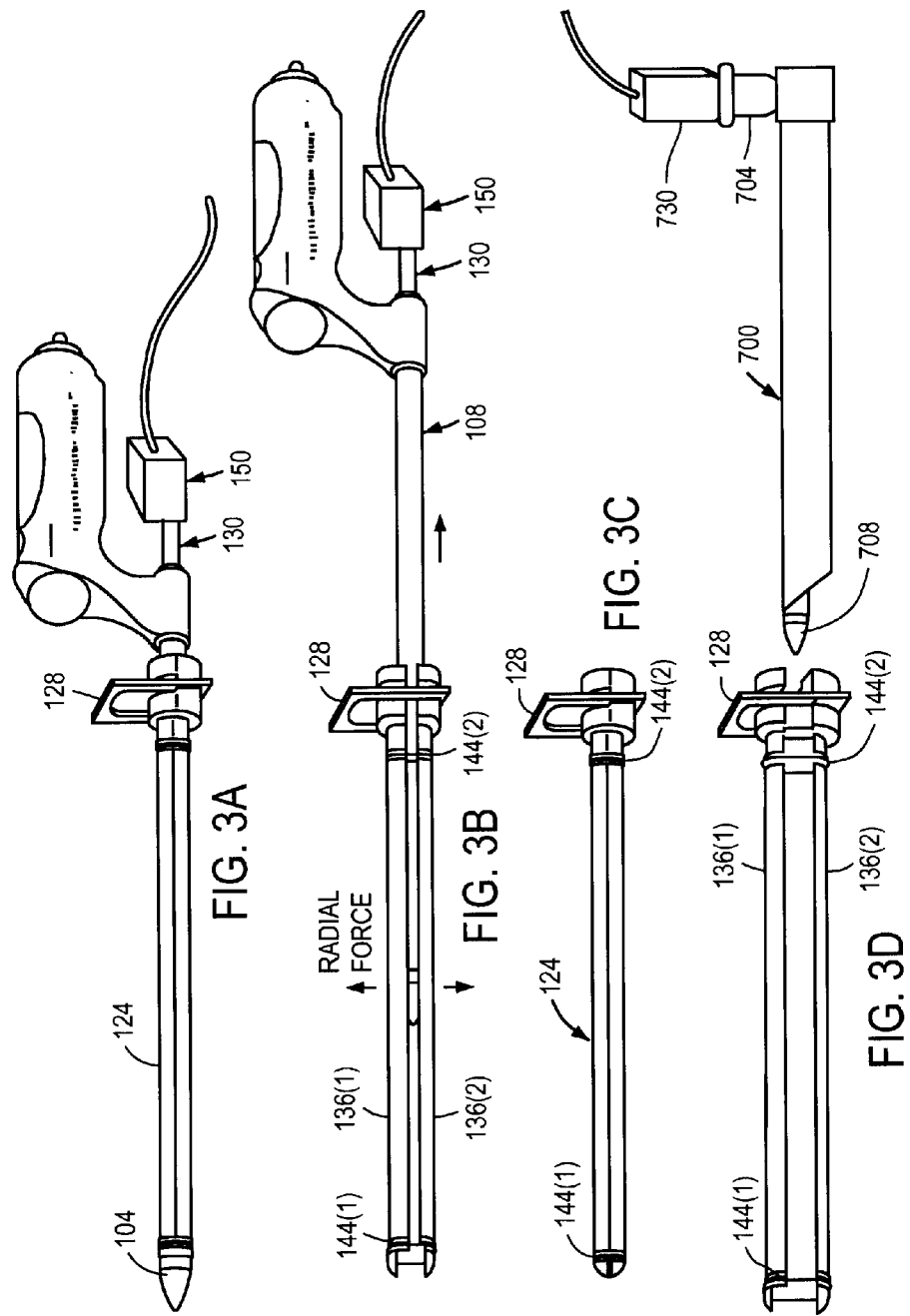
FIGS. 3A-D are perspective views illustrating the dilation tool in operation in accordance with the present invention.

In step 212, following advancement of the dilation tool 100 to the desired position in the body, expandable sheath 124 is held in place as inner cannula 108 is retracted through expandable sheath 124, as shown in FIG. 3B. Retraction of inner cannula 108 with enlarged region 118 through the length of expandable sheath 124 dilates the tissue adjacent to the length of expandable sheath 128 to at least the maximal dimension of the enlarged region 118. Preferably, the surgeon holds slide mount 128 in place, while pulling back on inner rigid cannula 108. The proximal taper 116 of cannula tip 104 rides against the chamfered inner surface of the distal end of the expandable sheath 128, smoothing out the initial process of cannula removal.

The inner cannula tip 104 glides along the outer edges of the two shells 136 during cannula withdrawal. The generally rigid structure of the split shells radially displaces the surrounding tissue as the shells part or separate, thus dilating the cavity initially created by advancement of dilation tool 100 as shown in step 212. Thus, substantially all of the force resulting from withdrawing cannula tip 108 is exerted on the edges of the shells 136, and not on the tissue. Shear force has the tendency of causing vessel avulsion and tissue abrasion, and its avoidance during dilation is preferable. However, in accordance with the present invention, only radial force is exerted on the tissue by the split shells 136, which reduces any trauma to the tissue from the dilation process. The dilation of the cavity facilitates subsequent insertion into the lumens of larger diameter instruments, particularly the endoscopic cannula of the present invention, as shown in step 216.

In one embodiment, expandable sheath 124 remains in position within the patient's body (not shown) in the dilated cavity created by removing inner cannula 108 as shown in FIG. 3B. In step 216, large diameter instruments are sequentially inserted through the proximal end of expandable sheath 124, without exerting shear force on the tissue cavity. Expandable sheath 124 accommodates instruments of varying diameters and cross-sections. Additionally, leaving expandable sheath 124 in place maintains a dilated cavity to the desired surgical site, thus facilitating the advancement of the next instrument to be used in the procedure to the correct position within the body. FIG. 3D illustrates an endoscopic cannula 700 according to the present invention about to be inserted into expandable sheath 124, which is expanded as shown in FIG. 3D to accommodate the larger diameter of the endoscopic cannula.

Advancement of the larger cannula dilates the dissection cavity to the exact size necessary to accommodate the larger cannula. Therefore, in accordance with the present invention, the cavity is dilated no larger than required to accommodate the surgical tools used in the procedure. In the prior art, a surgeon would have to estimate the amount of dilation required for a procedure, and would have to repeatedly dilate the tunnel if the surgeon underestimated the amount of dilation required. Conversely, over-estimating the amount of dilation required leads to unnecessary trauma. This is avoided through the use of the expandable sheath 124 which expands concurrent with the size of the tool inserted.

In another embodiment, the expandable sheath 124 is slidably attached to the inner cannula 108. In this embodiment, the inner cannula 108 is retracted through the expandable sheath 124 as described above, but the expandable sheath 124 remains positioned at the distal end of the dilation tool 100. After dilation has been achieved using the expandable sheath 124, the entire dilation tool 100 is removed from the body.

Figure 7A:
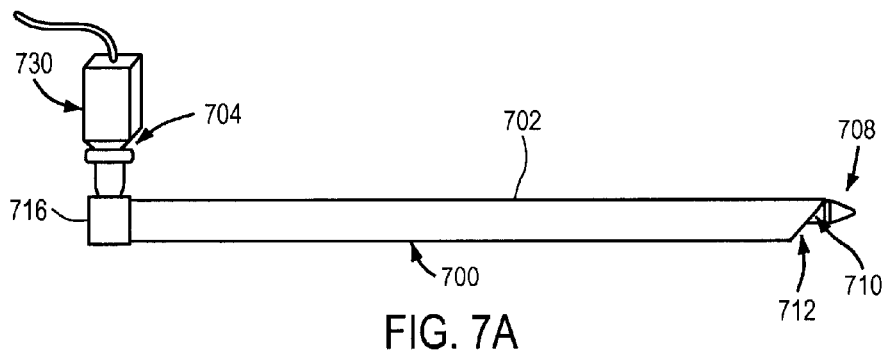
FIG. 7A is a perspective view of an endoscopic cannula with an access port in accordance with the present invention.

As previously mentioned, dilation tool 100 will be generally used with a larger diameter instrument, for facilitating the insertion of the larger diameter instrument by dilating a cavity to the surgical site within the patient's body. One such larger diameter instrument is an endoscopic cannula according to the present invention. Referring now to FIGS. 7A-D, endoscopic cannula 700 comprises cannula 702, having an elongated body and defining one or more lumens, 716 and 718. One of the lumens may be used as an endoscopic lumen 716 to house the endoscope, while the other lumen 718 is used as an access port for housing surgical devices, advanced either concurrently or sequentially, as will be discussed more specifically below. Endoscopic cannula 700 further comprises transparent tip 708 positioned at a distal end of cannula 702, and an endoscope 720 for visualization of the surgical procedure. Tip 708 is preferably tapered, and most preferably cone shaped, as shown in FIG. 7A. Cannula 702 may be constructed in any suitable configuration. For example, it may be constructed of a solid bar that is pierced to create lumens 718 and 716. Alternatively, cannula 702 preferably contains a smaller diameter dissection shaft 710 defining lumen 716, the shaft 710 terminating in tip 708 at its proximal end.

In a preferred embodiment, endoscope 740 is used with an eyepiece 704 skewed at a right or oblique angle to endoscope 740 to allow eyepiece 704 to be positioned away from the plane in which access port 718 resides. This arrangement prevents interference between a video camera 730 (attached to the eyepiece 704 of the endoscope) and a handle of a pericardial entry instrument (not shown). FIG. 7A illustrates endoscopic cannula 700 housing an eyepiece 704 at a right angle to endoscope 740. By positioning eyepiece 704 at a right angle to endoscope 740, rigid instruments may be inserted through access port 718 without interfering with camera 730. Alternatively, eyepiece 704 may be oriented along the longitudinal axis of endoscope 740. If eyepiece 704 is oriented in this alternative position, flexible instruments are inserted through access port 718 to avoid interfering with camera 730. The tapered profiles of these devices may render subxiphoid dissection to the pericardial surface sufficiently atraumatic to avoid the need for using dilation tool with an expandable sheath (shown in FIG. 1A) prior to advancement of the endoscopic cannula with an access port (shown in FIG. 7A).

The endoscope is approximately 4-5 mm in diameter, and the access port 718 is approximately 7 mm in diameter.

Access port 718 is sufficiently wide to permit the introduction of the necessary surgical tools for the operation. Endoscope 740 in the endoscopic cannula 700 is sealed inside a transparent tapered tip 708, preserving visualization as the endoscopic cannula 700 comes in contact with tissue fluid, blood, or pericardial fluid.

Figure 7B:
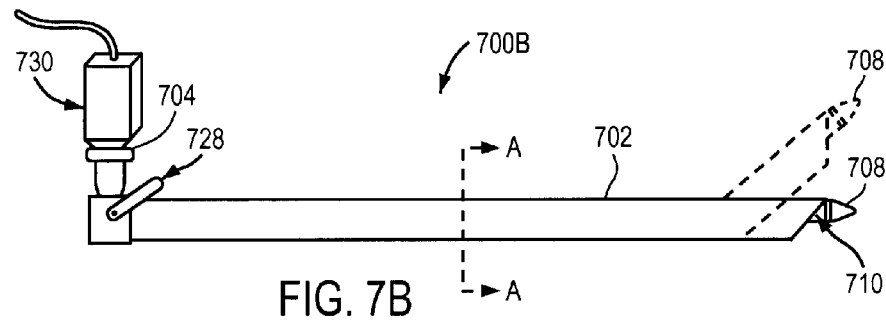
FIG. 7B is a perspective view of an endoscopic cannula with an access port with an articulatable head in accordance with the present invention.
Figure 7C:
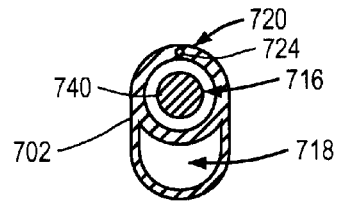
FIG. 7D is a perspective view of an endoscopic cannula that is substantially arcuate in shape.
Figure 7D:
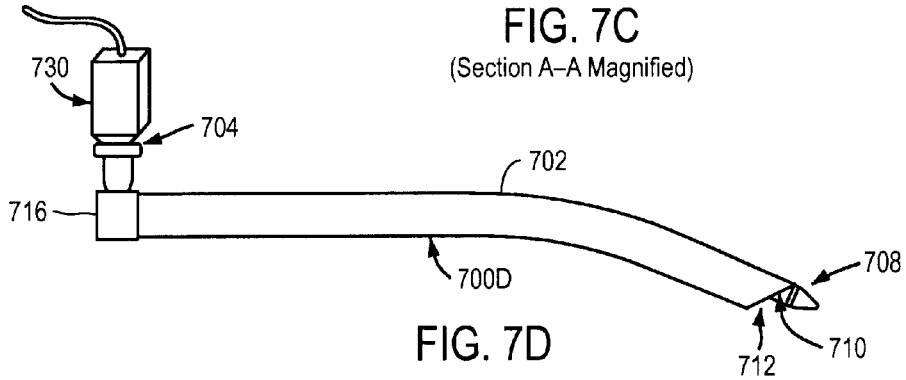

Preferably, endoscopic cannula 700 is substantially straight as shown in FIG. 7A and is constructed of a rigid material, such as metal or resilient plastic, to allow the creation of a cavity by blunt dissection resulting from advancement of the cannula within the body. Endoscopic cannula 700 may have any suitable profile, for example elliptical (as shown in FIG. 7C) or circular. In an alternative embodiment as shown in FIG. 7D, the endoscopic cannula 700D is rigid but substantially arcuate in shape. In another alternative embodiment, illustrated by articulating cannula 700B in FIG. 7B, the endoscopic cannula is constructed of a flexible material, such as flexible plastic (polyethylene, polyurethane, polytetrafluoroethylene, etc.) and its tip 708 is articulable, for example by a wire 720 running through a separate wire lumen 724 and attached to the distal end of the device, as shown in FIGS. 7B and 7C. Tensioning the wire 720 at its proximal end causes the cannula tip 708 to bend. Use of a flexible fiberoptic endoscope and a flexible endoscopic instrument in an articulating cannula 700B allows access into tight regions.

Figure 4:
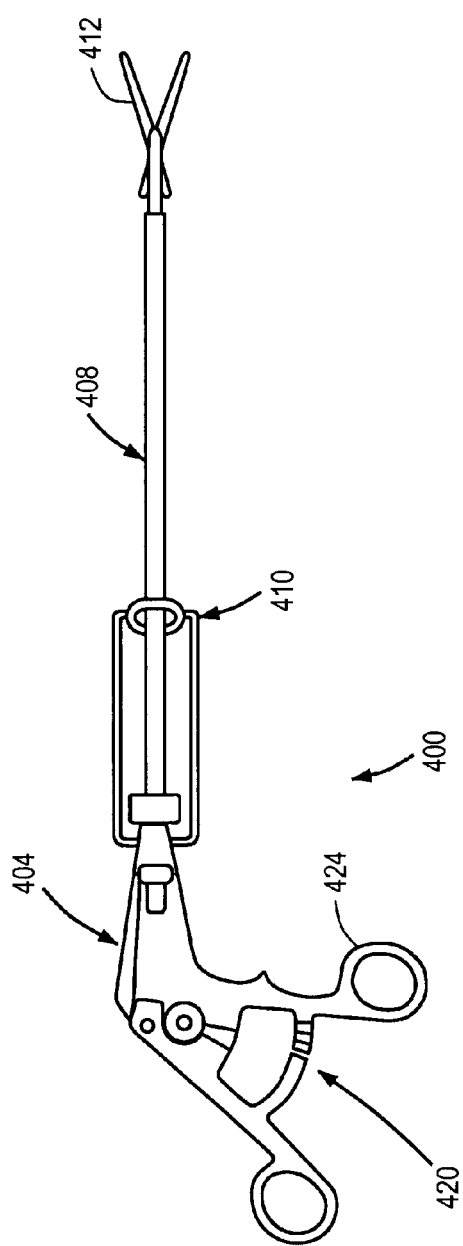
FIG. 4 is a perspective view illustrating a pericardial entry instrument in accordance with the present invention.

As previously discussed, endoscopic cannula 700 is used in conjunction with surgical instruments, which are inserted either concurrently or sequentially into an access port lumen of the endoscopic cannula. One such surgical instrument is the pericardial entry instrument of the present invention. FIG. 4 illustrates a perspective view of a preferred embodiment of pericardial entry instrument 400. The instrument 400 includes a grasping tool 404 and a cutting tool 408. The grasping tool 404 preferably comprises a pair of locking endoscopic grasping forceps 412 of approximately 5 mm diameter, as smaller diameter forceps may not provide sufficient force to dissect fatty tissue adherent to the pericardium, and to grasp the pericardium during cutting. Upon access to the pericardium, the grasping jaws 412 of the grasping tool 404 pinch together pericardial tissue to create a flap of pericardium. The cutting tool 408 is then extended out to cut the gripped flap of pericardium, creating a small opening within which other surgical instruments may be introduced. The cutting tool 408 is preferably a tubular cutter placed concentrically about a shaft of the grasping tool 404, having a sharpened distal edge. The tubular cutter 408 is disposed to facilitate free rotation about the shaft of the grasping tool 404, to facilitate the cutting of the pericardial tissue. The tubular cutter 408 is also slidably disposed on the shaft of the grasping tool 404 to facilitate axial translation from an initial position proximal to the grasping jaws 412 of the grasping tool 404 to a final position a short distance distal to the distal end of the grasping jaws 412 sufficient for cutting the pericardium.

In one embodiment, an extension limiter 410 is disposed near the proximal end of the instrument 400 to restrict the range of axial translation of the cutting tool 408. The extension limiter 410 allows the surgeon to push the cutting tool 408 forward without fear of accidentally advancing the cutting tool 408 through the pericardium. into the underlying heart. The cutting tool 408 cuts a small (approximately 5 mm diameter) hole in the pericardium responsive to being advanced into the gripped flap and being rotated upon contact. The procedure is preferably performed under direct vision through endoscopic visualization to avoid injury to the heart, which lies in contact with the inner surface of the pericardium.

The pericardial entry instrument 400 also includes a ratchet lock 420. The ratchet lock 420 is disposed as a part of scissor handle 424. When scissor handle 424 is closed, the grasping tool jaws 412 are closed. The ratchet lock 420 locks the jaws 412 into their closed position when the scissor handle 424 is closed. This allows the flap of pericardial tissue to be held securely while the cutting tool 408 is advanced into the tissue.

Figure 5:
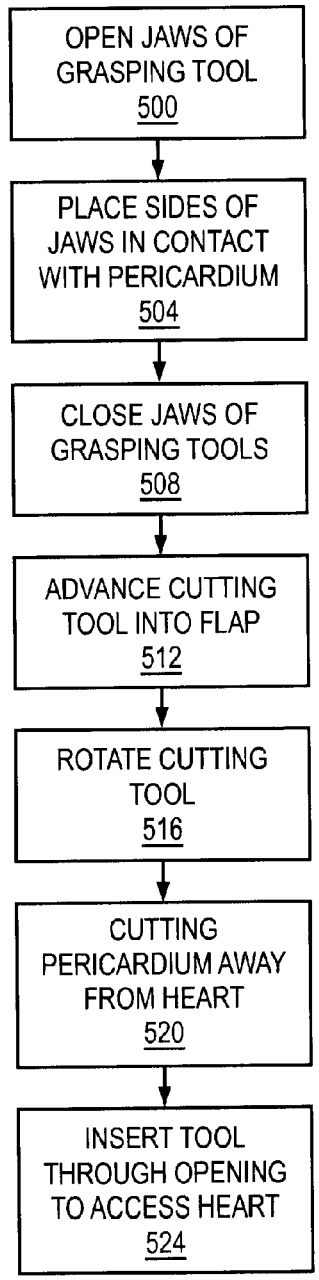
FIG. 5 is a flowchart illustrating a method of using the pericardial entry instrument in accordance with the present invention.
Figure 6A:
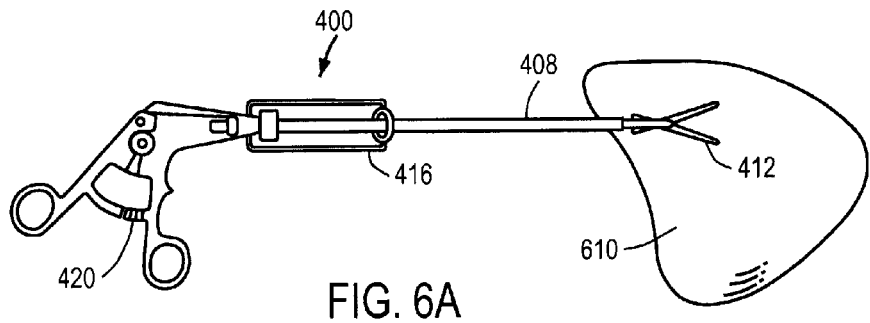
FIGS. 6A-D are perspective views illustrating the operation of the pericardial entry instrument in accordance with the present invention.
Figure 6B:
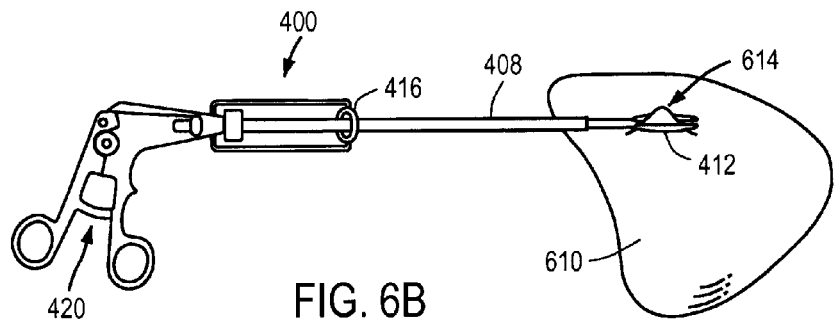
Figure 6C:
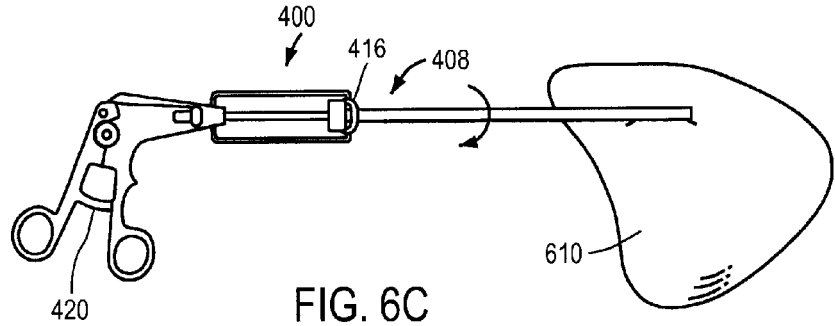

FIG. 5 is a flowchart which illustrates a method of using the pericardial entry instrument 400, as described with reference to FIGS. 6A-6D. In steps 500 and 504, the jaws 412 of the grasping tool 404 are opened, and the sides of the open jaws 412 are placed in contact with the pericardium 610, as shown in FIG. 6A. Jaws 412 are closed in step 508 to tent up a fold 614 of pericardium 610 as shown in FIG. 6B, while the underlying epicardial surface slips away from the grasp of the jaws 412, preventing pinching of the heart. Ratchet lock 424 is activated when the grasping tool jaws 412 is closed, and holds the pericardial fold 614 securely. Cutting tool 408 is advanced in step 512 toward the fold and is rotated simultaneously in step 516 to cut an opening 615 in the tented fold 614 of the pericardium, as shown in FIG. 6C. The pericardium 610 is grasped along the side of the grasping tool jaws 412, to facilitate tangential movement of the cutting tool 408 with respect to the surface of the heart. Therefore, the tented fold 614 of pericardium is cut in step 520 in a direction away from the underlying heart, ensuring that no injury occurs to the heart.

In the pericardial entry instrument 400, application of the forceps jaws in a tangential relationship to the surface of the heart at the site of pericardial entry ensures that no injury occurs to the heart. The cutting tool is in intimate contact with the forceps jaws. As it slices through the flap of pericardium held in the jaws, the cutting tube also lies tangential to the surface of the heart, and the surface of the heart is moved away without being cut. In contrast, if the pericardium were to be grasped by the distal tips of the forceps jaws, advancement of the cutting tool would occur in a direction perpendicular to the surface of the heart. Entry into the heart muscle would be much more likely.

Figure 6D:
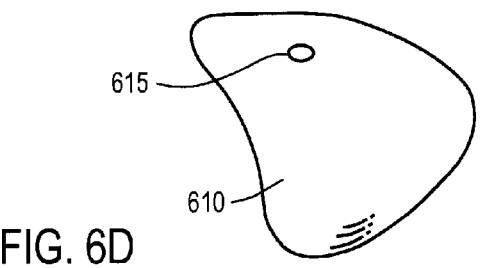

As shown in FIG. 6D, a small opening 615 with a cleanly cut edge is thus formed in the pericardium 610. Using endoscopic cannula 700 as previously described, surgical tools may be inserted via an access port of the endoscopic cannula through the opening 615 to access the heart in step 524 and perform the desired therapeutic procedure. The desired surgical and therapeutic procedures which can be performed at this point include but are not limited to such procedures as epicardial mapping and ablation for atrial and ventricular arrhythmias, pericardial window, myocardial biopsy, intrapericardial drug delivery, inserting a needle to inject cardiac muscle cells or undifferentiated satellite cells for cellular cardiomyoplasty, inserting a cannula to inject pharmacological agents for angiogenesis, robotic, cutting, stabilizing and anastomotic instruments for performing coronary artery bypass or coronary artery bypass grafting, or positioning a laser or other energy probe or mechanical piercing element to pierce the heart muscle for transmyocardial revascularization. In addition, the atrial appendage may be ligated and transected to prevent release of emboli in atrial fibrillation, for example by advancing a suture loop through the endoscopic cannula to cinch off the atrial appendage to prevent blood clots which frequently form in the appendage from migrating out and travelling to the brain.

Once a hole has been formed in the pericardium, the cannula may be advanced through the hole to access the heart. The pericardial entry instrument may be removed from the working lumen, and a variety of instruments may be inserted through the working lumen to perform procedures on the heart. For example, an electrode may be advanced through the working lumen to perform epicardial ablation for cardiac arrhythmias, including atrial fibrillation or ventricular tachyarrhythmias. A radiofrequency probe or a simple mechanical probe may be used to pierce the myocardium in multiple sites for transmyocardial revascularization (TMR). A needle may be advanced through the working lumen to inject undifferentiated muscle cells into infracted areas of the heart for the procedure of cellular cardiomyoplasty. Angiogenic pharmacologic agents may be injected into the myocardium. Devices may be inserted through the working lumen. A cardiac reinforcement device, for example as described in U.S. Pat. Nos. 6,077,218 and 6,085,754 to Alferness (incorporated herein by reference) and improvements thereof, may be inserted through the working lumen to surround the heart and restrict its volume in congestive heart failure. A linear stapler or a suture loop may be applied to the base of the atrial appendage, to seal off its opening and prevent ejection of blood clot into the cerebral circulation in patients with chronic atrial fibrillation.

In the above procedures, the transparent tip 104 performs a dual role. First, it retracts the pericardium from the epicardial surface of the heart, to allow visualization of the instrument inserted through the working lumen. Second, it allows continuous endoscopic visualization of the desired area of the heart, as the instrument is guided to perform the respective cardiac procedure.

Figure 8A:
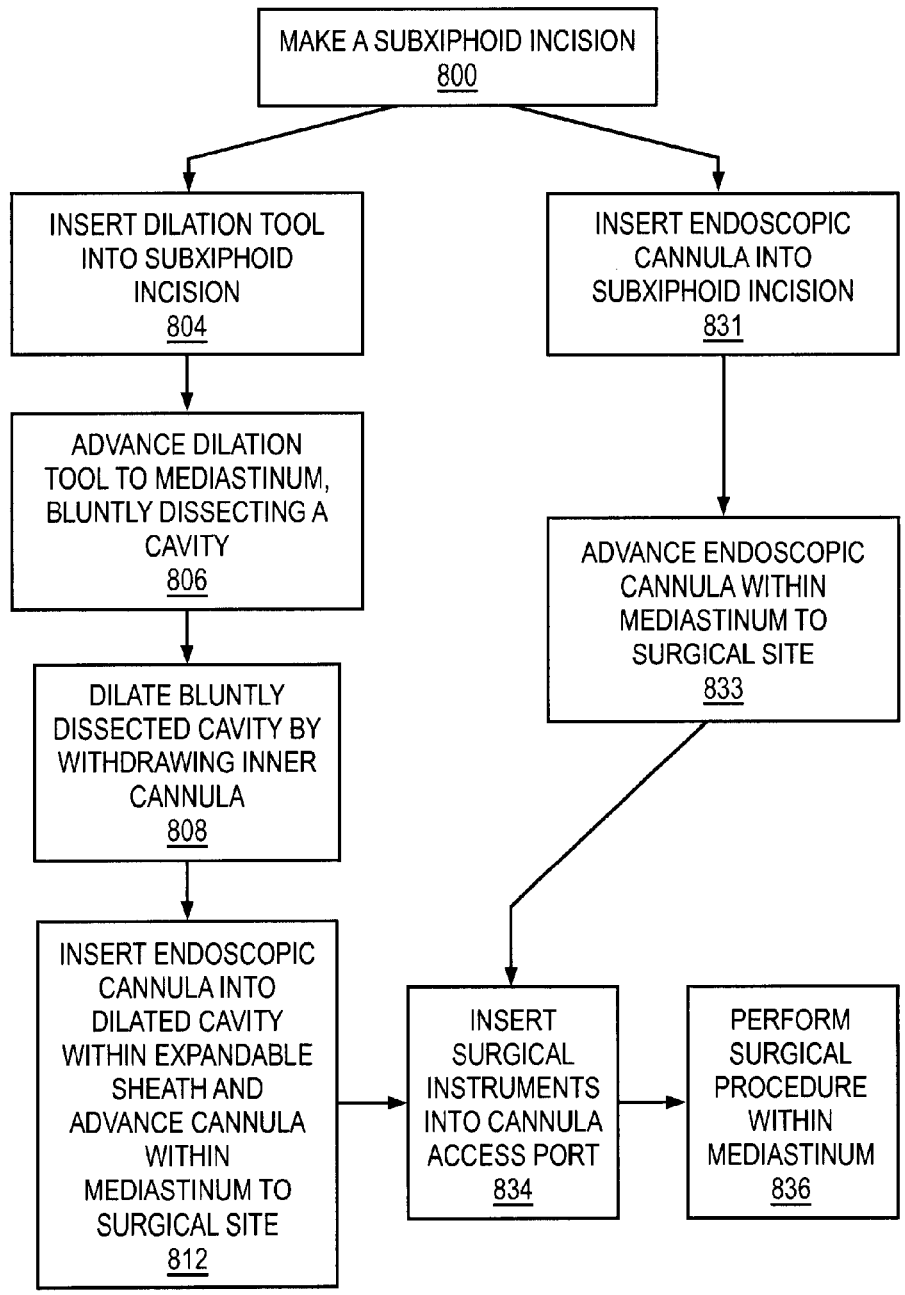
FIG. 8A is a flowchart illustrating the subxiphoid access method of using an endoscopic cannula via a dilated cavity using the dilation tool with an expandable sheath in accordance with the present invention, as well as an alternative method of using the endoscopic cannula and pericardial entry instrument in accordance with the present invention, without first dilating a cavity, for procedures performed within the mediastinum.
Figure 8B:
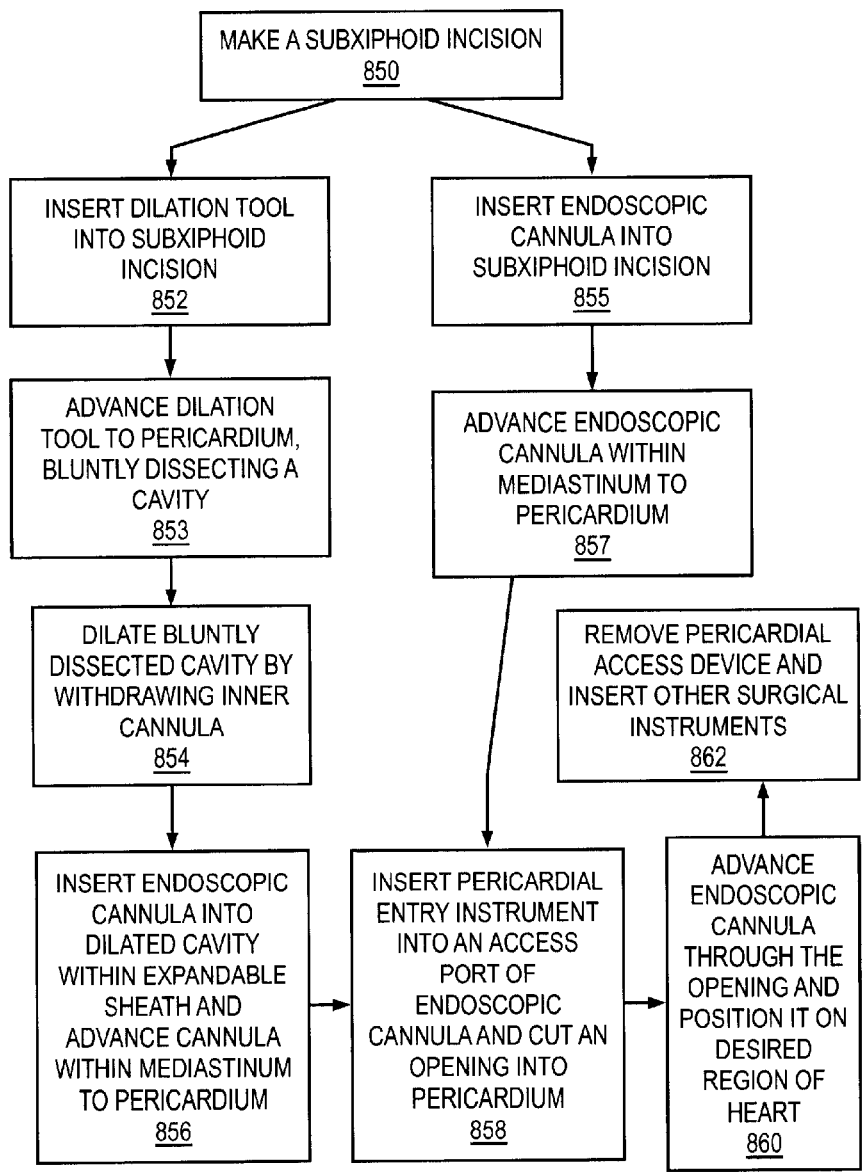
FIG. 8B is a flow chart illustrating two alternative methods of using an endoscopic cannula and pericardial entry instrument of the present invention, for procedures performed within the pericardium.
Figure 9A:
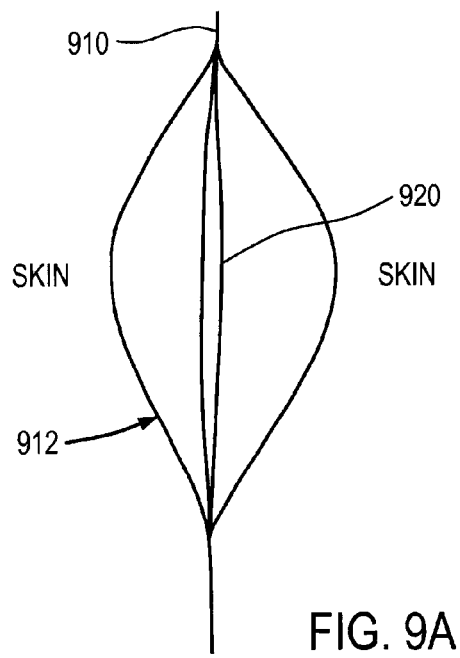
FIGS. 9A-D are partial cross sectional views of the operation of an endoscopic cannula and dilation tool in accordance with the present invention.
Figure 9B:
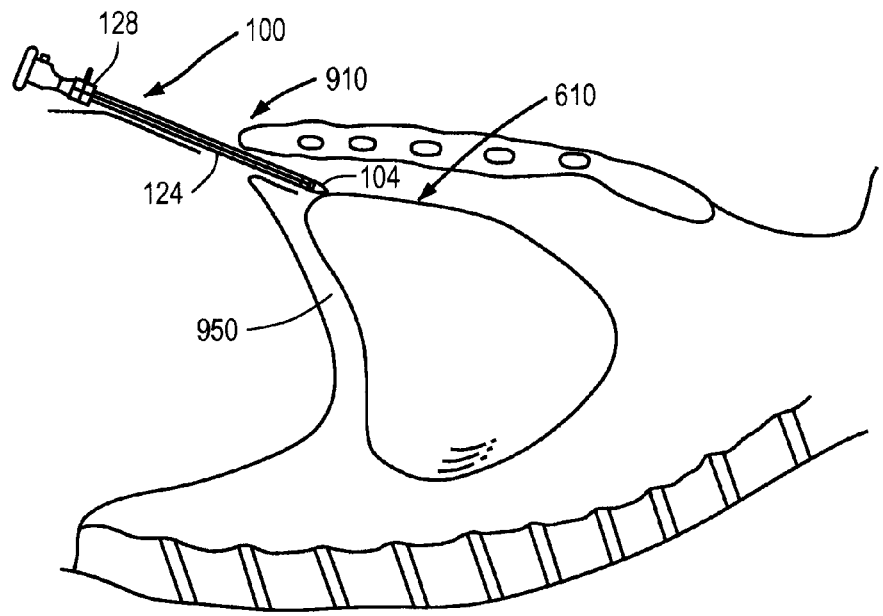

FIGS. 8A and 8B illustrate methods of performing surgical procedures using the devices described above, and will be described with reference to FIGS. 9A-D and 10A-D. FIGS. 8A and 9A-D illustrate a method of performing surgery on mediastinal structures in accordance with the present invention. In step 800, an incision 912 is made below the xiphoid process 910 (referred to as a subxiphoid incision) overlying the entry site, and the linea alba 920 is incised according to conventional practice, as shown in FIG. 9A. Next, in step 804, dilation tool 100 of the present invention is inserted into the subxiphoid incision under endoscopic visualization. In step 806, dilation tool 100 is advanced to the mediastinum 950 under endoscopic visualization, as shown in FIG. 9B. Advancement of dilation tool 100 causes tapered tip 104 to bluntly dissect a cavity responsive to the advancement of dilation tool 100. Dilation tool 100 is then positioned within the bluntly dissected cavity in the mediastinum 950 on the posterior aspect of the xiphoid process and sternum, for example to a position with tip 104 facing the pericardium 610 (but alternatively to a position in which tip 104 faces another organ within the mediastinum) as shown in FIG. 9B.

Figure 9C:
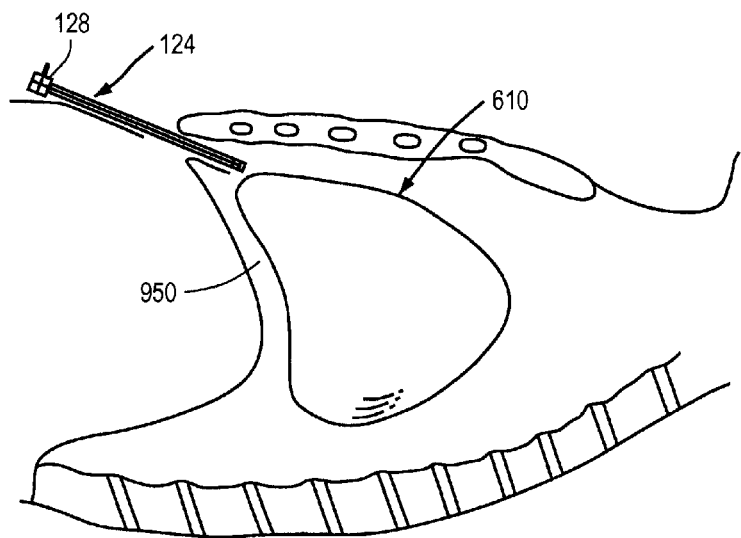

As the dilation tool 100 has a relatively small diameter, its use before the advancement of larger diameter instruments minimizes the risk of trauma to the surgical site. In step 808, the bluntly dissected cavity created in steps 804 and 806 is dilated by withdrawing inner cannula 108 through expandable sheath 124 of dilation tool 100, leaving sheath 124 in place as shown in FIG. 9C. Retraction of inner cannula 108 with enlarged region 118 through the length of expandable sheath 124 dilates the tissue adjacent to the length of expandable sheath 128 to at least the maximal dimension of the enlarged region 118. Preferably, the surgeon holds rigid slide mount 128 in place, while pulling back on inner rigid cannula 108. The proximal taper 116 of cannula tip 104 rides against the chamfered inner surface of the distal end of the expandable sheath 128, smoothing out the initial process of cannula removal.

The generally rigid structure of the split shells radially displaces the surrounding tissue as the shells part or separate, thus dilating the cavity initially created by advancement of dilation tool 100. Thus, substantially all of the force resulting from withdrawing cannula tip 108 is exerted on the edges of the shells 136, and not on the tissue. Shear force has the tendency of causing vessel avulsion and tissue abrasion, and its avoidance during dilation is preferable. However, in accordance with the present invention, only radial force is exerted on the tissue by the split shells 136, which reduces any trauma to the tissue from the dilation process. The dilation of the cavity facilitates subsequent insertion into the lumens of larger diameter instruments, particularly the endoscopic cannula of the present invention, as shown in FIG. 9C.

Figure 9D:
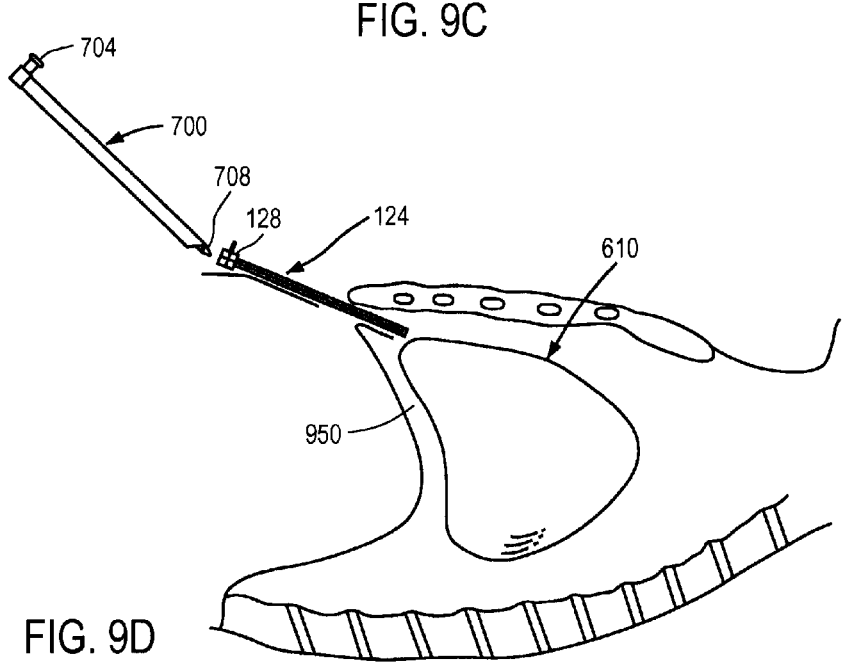

As shown in FIG. 9C, expandable sheath 124 stays in place after withdrawing inner cannula 108. In step 812, a larger diameter instrument, for example the endoscopic cannula 700 of the present invention, is inserted into the cavity dilated by expandable sheath 124, as shown in FIG. 9D. In step 834, surgical instruments are inserted into the one or more access ports of endoscopic cannula 700, for example access port 718 as shown in FIG. 7C. In step 836, surgical procedures are then performed within the mediastinum 950 on the desired mediastinal organ. Typical surgical procedures that may be performed in the mediastinum include, for example, ablation and biopsy of lymphatic glands, thymectomy (removal of thymus gland), tracheal and esophageal repair. Typical surgical instruments that may be inserted for operation in the mediastinum include ablation catheters, radiofrequency or cryogenic probes, biopsy needles, and endoscopic graspers, shears and needle holders.

Figure 10A:
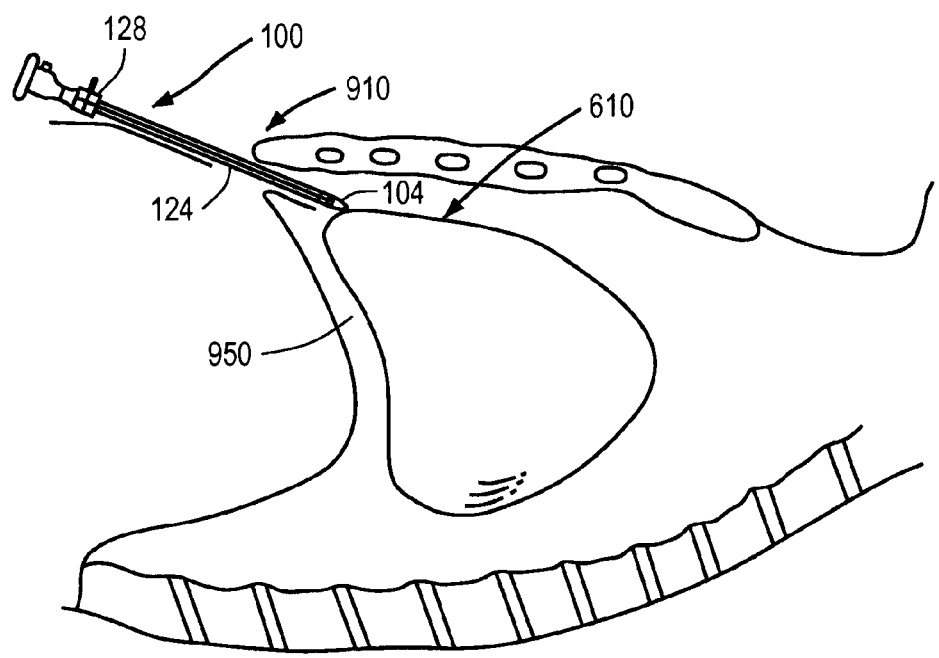
FIGS. 10A-E are partial cross sectional view of the operation of an endoscopic cannula, dilation tool and pericardial entry instrument in accordance with the present invention.
Figure 10B:
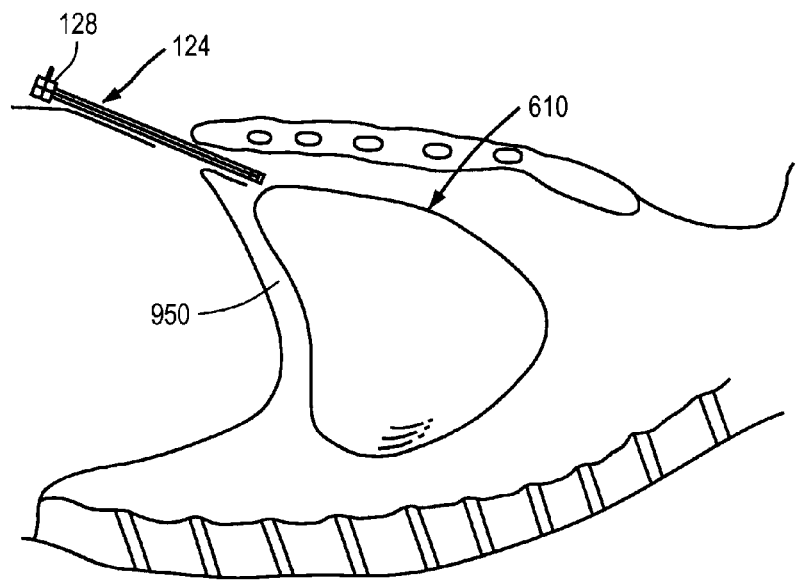
Figure 10C:
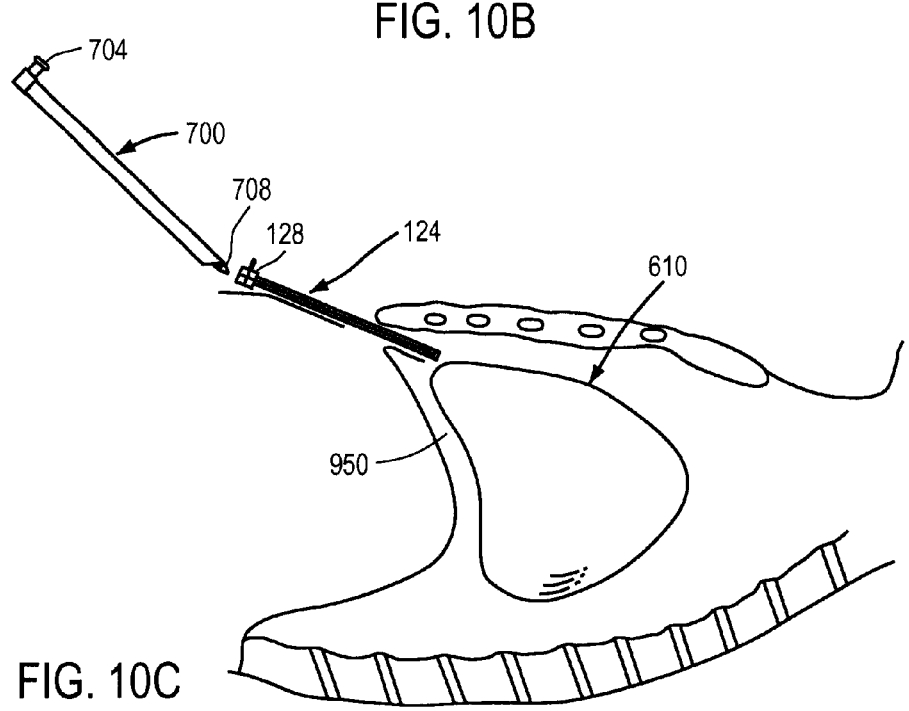

Alternatively, the mediastinum 950 may be accessed without initially dilating a cavity using dilation tool 100, as shown in the alternative flow chart in FIG. 8A. In step 800, a subxiphoid incision is made overlying the entry site, and the linea alba 920 is incised according to conventional practice. Next, in step 831, a larger diameter surgical tool (for example the endoscopic cannula 700 of the present invention) is inserted into the subxiphoid incision and positioned in the mediastinum on the posterior aspect of the xiphoid process and sternum. In step 833, the larger diameter surgical tools is advanced in the mediastinum 950 to the surgical site of interest under endoscopic visualization, bluntly dissecting a cavity responsive to the its advancement. In step 834, surgical instruments are inserted into an access port of the larger diameter surgical tool, for example access port 718 of the endoscopic cannula 700 of the present invention. The surgical instruments may be advanced either concurrently or sequentially, that is a first instrument can be inserted, used, then retracted, and then a second instrument inserted, used, and retracted, etc. Finally, in step 836, the surgical procedure is performed within the mediastinum 950 on the desired mediastinal organ.

Where the mediastinal organ of interest is the heart (situated within the pericardium), the method is generally as described above until the larger diameter instrument reaches the pericardium. Referring now to FIGS. 8B and 10A-E and 11A, in step 850 a subxiphoid incision is made and the linea alba is incised according to conventional practice, as shown in FIG. 9A. In step 852, dilation tool 100 is inserted into the subxiphoid incision under endoscopic visualization as shown in FIG. 10A, and a cavity is bluntly dissected during its advancement in step 853. In step 854, the cavity is dilated as previously described using the dilation tool as shown in FIG. 10B. In step 856, the larger diameter instrument (for example endoscopic cannula 700 of the present invention) is advanced within the mediastinum 950 toward the pericardium through the dilated cavity under endoscopic visualization as shown in FIG. 10C. Alternatively, in steps 855 and 857 the endoscopic cannula is advanced directly into the subxiphoid incision without first dilating the bluntly dissected cavity.

Figure 10D:
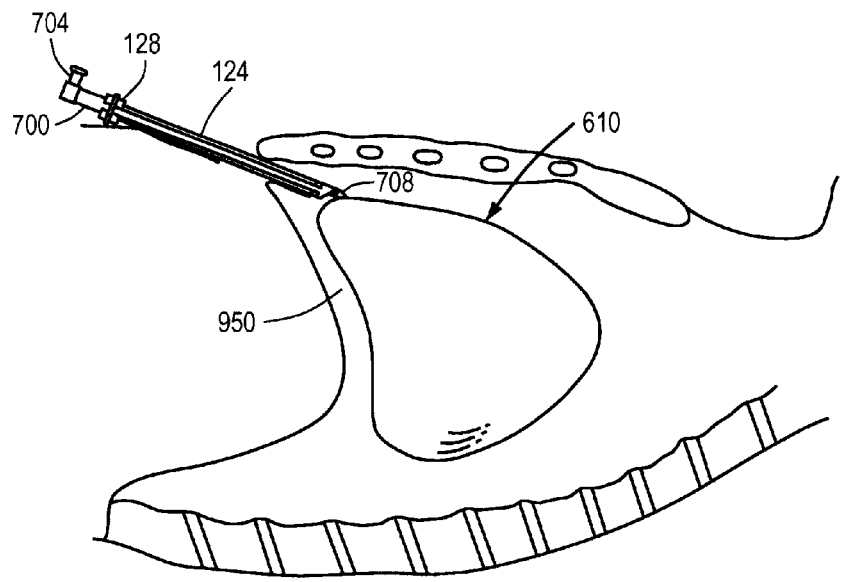
Figure 10E:
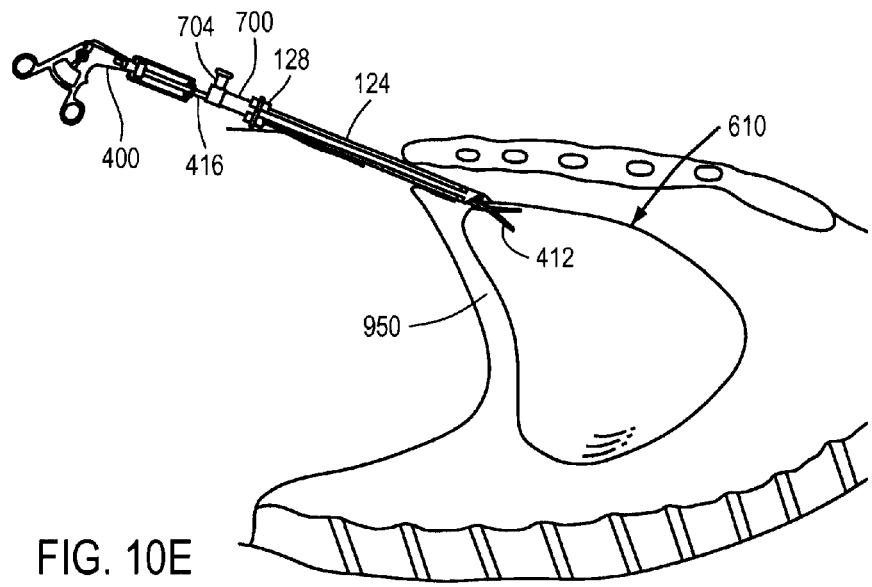
Figure 11A:
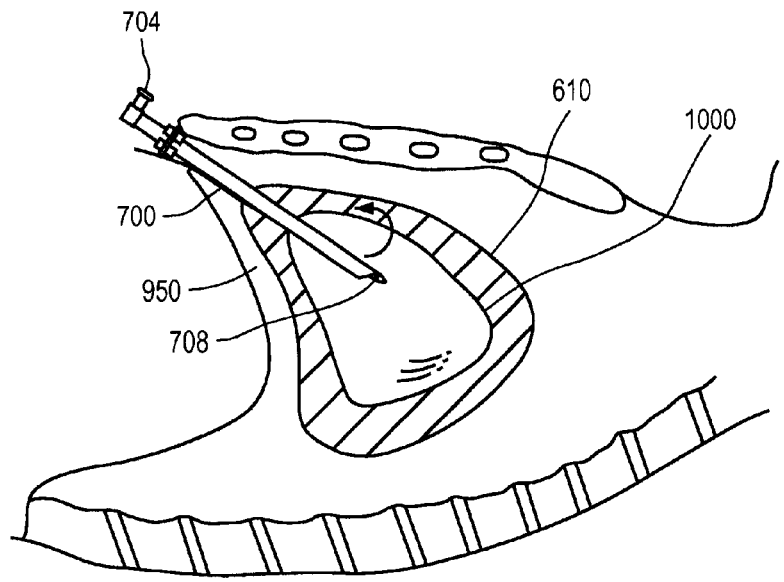
FIGS. 11A-C are partial cross sectional views illustrating 360° access to the heart using the subxiphoid access method of this invention.

Upon reaching the pericardium as shown in FIG. 10D, in step 858 an opening is cut in the pericardium using the pericardial entry instrument as previously described (FIG. 10E). Specifically, as shown in FIG. 4, the anterior pericardium is grasped with pericardial entry instrument 400 to lift the pericardium away from the heart. Tubular cutter 408 is then rotated to create a controlled cut of the pericardium, creating opening 615. In step 860, endoscopic cannula 700 is advanced through the opening and is positioned on the desired region of the heart under endoscopic visualization (FIG. 11A). Preferably, opening 615 is made near the apex of the pericardium and endoscopic cannula is initially advanced from the apex toward the base of the heart. The left anterior descending coronary artery and the left atrial appendage provide landmarks for the surgeon so the location of the surgical site of interest is more easily found.

In step 862, pericardial entry 400 instrument is removed from access port 718 of endoscopic cannula 700, and other desired surgical instruments are inserted through access port 718 to operate on the heart within the pericardium. In an alternative embodiment, endoscopic cannula 700 includes more than one access port, such that removal of the pericardial entry instrument is not necessary for the insertion of other surgical instruments. In still another embodiment, the access port is of a sufficient size so that several surgical instruments may be inserted concurrently. The surgical and therapeutic operations which can be performed at this point include but are not limited to such procedures as epicardial mapping and ablation for atrial and ventricular arrhythmias, pericardial window, myocardial biopsy, intrapericardial drug delivery, inserting a needle to inject cardiac muscle cells or undifferentiated satellite cells for cellular cardiomyoplasty, inserting a cannula to inject pharmacological agents for angiogenesis, robotic, cutting, stabilizing, and anastomotic instruments for performing coronary artery bypass or coronary artery bypass grafting, or positioning a laser or other energy probe or mechanical piercing element to pierce the heart muscle for transmyocardial revascularization. In addition, the atrial appendage may be ligated and transected to prevent embolism in patients with chronic atrial fibrillation, for example by advancing a suture loop through the endoscopic cannula to cinch off the atrial appendage to prevent migration of blood clots which frequently form in the appendage from migrating out and travelling to the brain.

Figure 11B:
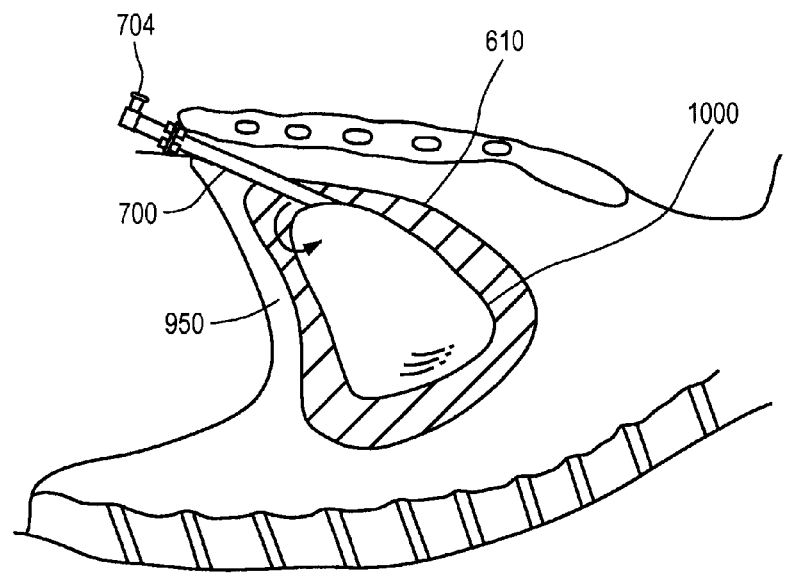
Figure 11C:
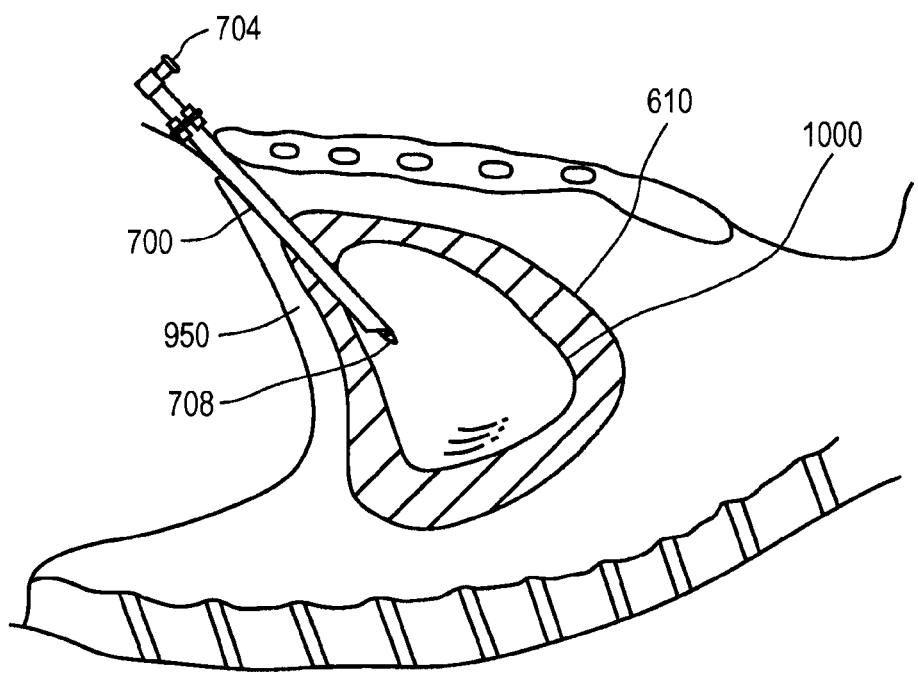

The subxiphoid pericardial access method as herein described is particularly advantageous as it enables the surgeon to access all regions of the heart, that is a 360 degree view including the anterior, posterior, left and right regions of the heart. Referring now to FIGS. 11A-C, endoscopic cannula 700 is initially inserted into the pericardium 610, preferably via an incision near the apex of the heart 1100, and then swept around the heart 1100 over the anterior and posterior surfaces of the heart 100 (e.g. from the position shown in FIG. 10A to that shown in FIG. 10B and then back to the position shown in FIG. 10C. As shown in FIGS. 11A-C, endoscopic cannula 700 is maneuvered around the heart 1100 in such a way that all regions of the heart may be accessed. The endoscopic cannula can be maneuvered because of the subxiphoid entry position and the flexibility of soft tissue around the heart, the softness of the tissue allowing the endoscopic cannula to push apart tissue and move around the heart. Thus, all regions of the heart may be accessed without the need for invasively lifting or rotating the heart to access posterior or lateral vessels and structures.

As described above, once a larger diameter instrument, for example endoscopic cannula 700, is inserted into the pericardium (either through a cavity dilated by expandable sheath 124, as shown in FIG. 9D, or without using an expandable sheath, as shown in FIGS. 11A-11C), surgical instruments are inserted into the one or more access ports of the larger diameter instrument, for example port 718 of endoscopic cannula 700 as shown in FIG. 7C.

The several apparatus of the various aspects of the present invention have been discussed in relation to a subxiphoid access surgical method. However, use of the apparatus disclosed herein, that is an endoscopic cannula, a dilation tool, and a pericardial entry instrument, and is not limited to use with the subxiphoid access method. While the subxiphoid access method is preferred because of its minimally invasive nature, other methods of access may also be used, for example using an incision in the intercostal region and advancing the endoscopic cannula through the incision to gain access to the pleural cavity. In such a procedure, the pleural membrane and the pericardial membrane, which lie in contact with one another, are grasped and punctured using the pericardial entry instrument to reach the heart. In addition, the methods described herein are not limited to accessing mediastinal structures (which includes the pericardium). For example, procedures requiring access to the peritoneum, the dura mater, or any membrane overlying a sensitive organ, for example, the spine, the brain, or the stomach, also benefit from the use of the apparatus and method described above.

What is claimed is:

1. A method of performing a cardiac procedure with a rigid cannula and a laterally expandable sheath, comprising the steps of:
   (a) incising skin overlying an entry point for the cardiac procedure;
   (b) inserting the rigid cannula disposed within the expandable sheath into the incision;
   (c) advancing the rigid cannula with the expandable sheath disposed thereon through tissue under endoscopic visualization to form a passage of dissected tissue between the incision and the pericardium; and
   (d) laterally expanding the sheath within the passage responsive to withdrawing the rigid cannula through the expandable sheath in a direction toward a proximal end thereof for dilating tissue along the passage to form a working cavity in dilated tissue along the passage.

2. The method of claim 1 in which the rigid cannula has a selected diameter and includes a distal tip of greater than the selected diameter, and wherein dilating the working cavity further comprises:
   laterally expanding the sheath responsive to the distal tip withdrawing with the rigid cannula through the sheath in a direction toward the proximal end thereof, leaving the expandable sheath positioned in the passage.

3. The method of claim 1 further comprising the step of:
   (e) additionally dilating the working cavity to larger lateral dimensions of the distal tip on the rigid cannula responsive to insertion into the expandable sheath positioned within the passage of a surgical tool having lateral dimensions larger than the distal tip on the rigid cannula.

4. The method of claim 2 further comprising the steps of:
   (e) inserting into a proximate end of the expandable sheath positioned within the passage an endoscopic cannula for performing a cardiac procedure in which the endoscopic cannula has a maximal lateral dimension greater than a maximal lateral dimension to which the sheath expanded in response to withdrawal therethrough of the distal tip of the rigid cannula;

(f) advancing the endoscopic cannula within the expandable sheath positioned within the working cavity toward a distal end thereof to laterally expand the expandable sheath and additionally dilate tissue in the working cavity; and (g) performing a cardiac procedure using the endoscopic cannula.

5. The method of claim 3 in which the surgical tool includes an endoscopic cannula.

6. A method of performing a cardiac procedure with a rigid endoscopic cannula and a laterally expandable sheath, comprising the steps of:

incising skin overlying an entry point for the cardiac procedure;

inserting the expandable sheath into the incision;

advancing the endoscopic rigid cannula within the expandable sheath under endoscopic visualization to form a passage of dissected tissue between the incision and the pericardium in response to the endoscopic cannula passing through the expandable sheath in a direction toward a distal end thereof to form a working cavity in dilated tissue along the passage; and performing a cardiac procedure through the endoscopic cannula.

* * * * *